(12) United States Patent
Single, Jr.

(10) Patent No.: US 8,215,309 B2
(45) Date of Patent: Jul. 10, 2012

(54) PERCUTANEOUS EMERGENT CRICOTHYROIDOTOMY AIRWAY DEVICE

(76) Inventor: Gordon W. Single, Jr., Queensbury, NY (US)

( * ) Notice: Subject to any disclaimer, the term of this patent is extended or adjusted under 35 U.S.C. 154(b) by 657 days.

(21) Appl. No.: 12/371,058

(22) Filed: Feb. 13, 2009

(65) Prior Publication Data

US 2009/0229602 A1 Sep. 17, 2009

Related U.S. Application Data

(60) Provisional application No. 61/064,097, filed on Feb. 15, 2008.

(51) Int. Cl.
*A61M 16/00* (2006.01)
(52) U.S. Cl. .............. 128/207.29; 128/207.14
(58) Field of Classification Search ........ 128/207.14–207.17, 207.29
See application file for complete search history.

(56) References Cited

U.S. PATENT DOCUMENTS

| | | | | |
|---|---|---|---|---|
| 3,759,263 | A | * | 9/1973 | Taylor ............... 128/207.29 |
| 3,991,765 | A | * | 11/1976 | Cohen ............... 128/207.29 |
| 4,520,810 | A | | 6/1985 | Weiss |
| 4,556,059 | A | * | 12/1985 | Adamson, Jr. ........... 128/207.29 |
| 4,617,929 | A | * | 10/1986 | Gill ..................... 606/108 |
| 4,677,978 | A | | 7/1987 | Melker |
| 4,889,112 | A | * | 12/1989 | Schachner et al. ....... 128/200.26 |
| 4,969,454 | A | | 11/1990 | Servello |
| 7,308,896 | B2 | * | 12/2007 | Cruz .................. 128/207.29 |
| 7,373,939 | B1 | * | 5/2008 | DuBois et al. .......... 128/207.29 |

* cited by examiner

*Primary Examiner* — Lynne Anderson
(74) *Attorney, Agent, or Firm* — Nixon Peabody LLP

(57) ABSTRACT

A percutaneous emergent cricothyroidotomy airway device for creating a surgical airway in a patient. The device includes a housing and a palm grip movably disposed in the housing between an expanded position and a compressed position. A first prong extends from the housing and second prong extends from the palm grip, wherein when the palm grip is in the expanded position, the first and second prongs are spaced apart and when the palm grip is moved to the compressed position the second prong is adjacent the first prong. A blade actuator is movably disposed in the housing. The blade actuator has opposed ends and a blade for puncturing a cricothyroid membrane of a patient is disposed on one end of the blade actuator. To create an airway an airway device of the present invention is provided. The palm grip is compressed to move the second prong adjacent the first prong. The blade actuator is actuated to advance the blade from between the prongs. Next, the blade is advanced through the cricothyroid membrane to make an incision. The blade is retracted and the first and second prongs are positioned within the incision in the cricothyroid membrane. The palm grip is then released to separate the first and second prongs to separate the tissue and form an airway.

39 Claims, 27 Drawing Sheets

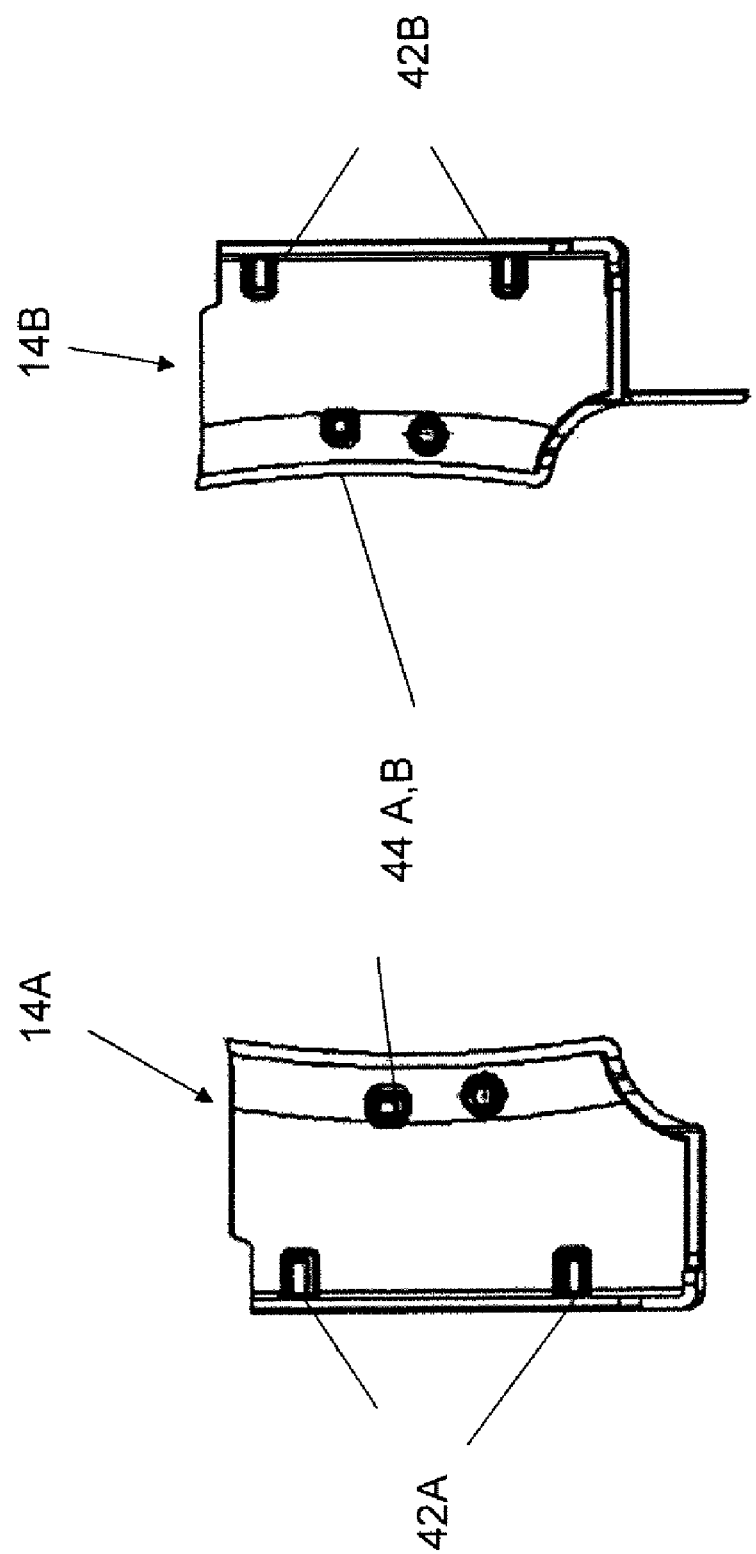

PERCUTANEOUS EMERGENT CRICOTHYROIDOTOMY AIRWAY DEVICE

CROSS-REFERENCE TO RELATED APPLICATIONS

This application claims priority under 35 U.S.C. §119 to U.S. Provisional Application Ser. No. 61/064,097, filed Feb. 15, 2008, which is incorporated herein by reference.

BACKGROUND OF THE INVENTION

1. Field of the Invention

The present invention relates to a percutaneous emergent cricothyroidotomy airway device (PECAD) and method for creating a surgical airway when the oral and/or nasal airway cannot be intubated.

2. Description of the Related Art

When a patient has any sort of severe injury, there is a requirement to maintain a reliable and stable airway to the lungs. When paramedics or other emergency professionals face unexpected difficulty in intubation, the main priority is to ensure adequate ventilation and provide the patient with the required level of oxygen needed for survival. Continuous attempts at orotracheal and or nasotracheal intubation can result in bleeding and edema of the upper airway, above the thyroid gland, making the process of tracheal intubation much more difficult and perhaps impossible.

After a few failed attempts, paramedics are advised to move on to a pre-planned failed intubation sequence, such as implementing a surgical airway. A surgical airway is usually performed when orotracheal intubation is unsuccessful or can not be performed. With current methods and devices on the market, there is a large risk associated to creating a surgical airway which makes this process preferably designated for emergency use only.

Some situations in which creating a surgical airway is necessary include major maxillo-facialary injury, oral burns, fractured larynx, or severe damage to the thoracic region. There are currently two methods of performing a surgical airway procedure, the needle or Silenger cricothyroidotomy method and the surgical or formal cricothyroidotomy method.

The Silenger cricothyroidotomy method involves percutaneously placing a relatively large gauge cannula needle into the trachea by penetrating through the cricothyroid membrane. Dilator sheaths are then placed over the needle, allowing the tissue circumventing the needle to expand. A breathing tube can then be inserted over the needle and sheath dilator assembly down towards the lungs. The needle and dilators are then removed giving the patient a temporary airway. See U.S. Pat. Nos. 4,677,978; 4,969,454. This method will allow adequate ventilation for up to 45 minutes. A risk of hypercapnea dictates the time constraint. In the past, this 45 minute time period would allow a patient to remain alive while in transport to a hospital where they were able to be converted to a formal tracheotomy.

A formal cricothyroidotomy or classic surgical airway has been proven in studies to be safer and quicker than performing a formal tracheotomy due to anatomical location and the precision required. The surgical cricothyroidotomy involves making an incision through the cricothyroid membrane, or ligament, and placing a tracheal tube down into the trachea through the hole made in the membrane. See U.S. Pat. No. 4,520,810.

The above is not the preferred technique for children under twelve due to the size of the anatomy. The gap between the cricoid and thyroid cartilage is much smaller in children then adults. Moreover, the cricothyroidotomy usually does not involve the use of local anesthetics due to time constraints and if a patient is asphyxiating, suffocating, or dying.

Some complications arising from the above procedures include but are not limited to: venus transaction, infection, unintended perforation, aspiration of gastric contents, and esophageal perforation. These complications can cause the following: hemorrhaging, decrease in blood pressure, cardiogenic shock, non healing of wounds, antibiotic treatment, extended rehabilitation in hospital, surgical resection, hypoxemia, bradycardia, hemodynamic collapse, cardiac arrhythmia, cardiac arrest, laryngo-tracheal complication, hoarseness, loss of voice, inflammation, pneumonia, gastric intestinal bypass surgery and/or death.

Thus, there is a need for a device that allows medical personnel to perform a cricothyroidotomy procedure faster and safer than conventional methods.

SUMMARY OF THE INVENTION

The cricothyroidotomy airway device of the present invention makes it easier for a paramedic/physician to percutaneously insert the device through the correct membrane, avoiding potentially serious complications to the patient.

The smaller blade profile of the device also reduces excess cutting that occurs during a surgical cricothyroidotomy. The device makes an incision just large enough to pass an endotracheal tube through. This reduces thoracic trauma, reducing post operative reconstruction and in-patient recovery time.

The present device is anticipated to take a fraction of the time it takes to implement one of the conventional methods. Within seconds of the device penetrating through the neck, the patient is able to breathe due to the device's spring open action.

Most make shift cricothyroidotomy devices need to be removed and converted to a standard tracheotomy upon admittance into the trauma center. The device of the present invention can be implemented and left in place for up to 24 hours, which will allow paramedics/physicians to focus their attention to the patient's other needs.

The small profile of the blade will only cut through enough of the cricothyroid membrane to pass an endotracheal tube through. Moreover, the device is designed only to penetrate through the front wall of the trachea reducing any risk of penetrating through the back wall of the trachea.

One aspect of the present invention is to provide a percutaneous emergent cricothyroidotomy airway device including a housing and palm grip movably disposed in the housing between an expanded position and a compressed position. A first prong extends from the housing and second prong extends from the palm grip, wherein when the palm grip is in the expanded position, the first and second prongs are spaced apart and when the palm grip is moved to the compressed position the second prong is adjacent the first prong. A blade actuator is movably disposed in the housing. The blade actuator has opposed ends and a blade for puncturing a cricothyroid membrane of a patient is disposed on one end of the blade actuator.

Another aspect of the present invention provides a method for creating a percutaneous emergent cricothyroidotomy airway including the steps of providing an airway device, the device having a housing, a palm grip movably disposed in the housing between an expanded position and a compressed position, a first prong extending from the housing, a second prong extending from the palm grip, wherein when the palm grip is in the released position the first and second prongs are spaced apart and when the palm grip is moved to the compressed position the second prong is adjacent thee first prong, a blade actuator movably disposed in the housing, the blade actuator having opposed ends, and a blade disposed between the first and second prongs for puncturing a cricothyroid membrane of a patient disposed on one end of the blade actuator; compressing the palm grip to move the second prong adjacent the first prong; actuating the blade actuator to advance the blade from between the prongs; advancing the blade through the cricothyroid membrane; retracting the blade; positioning the first and second prongs within the cricothyroid membrane; and releasing the palm grip to separate the first and second prongs to separate the tissue and form an airway.

These and other features, aspects, and advantages of the present invention will become more apparent from the following detailed description of the preferred embodiment relative to the accompanied drawings, in which:

BRIEF DESCRIPTION OF THE DRAWINGS

FIGS. 6A and 6B are side views of the housing sections.

DETAILED DESCRIPTION OF THE PREFERRED EMBODIMENTS

Figure 1:
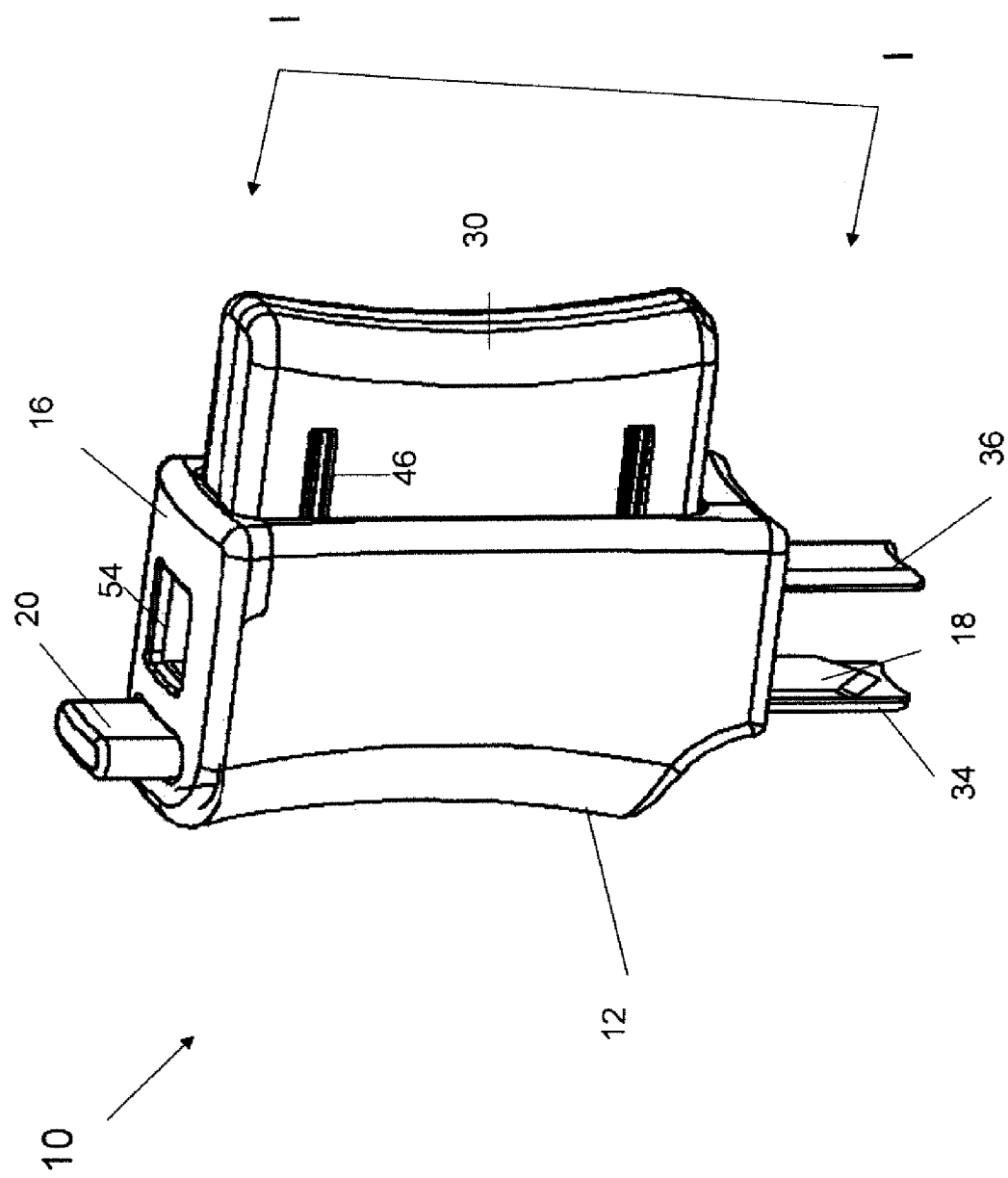
FIG. 1 is a perspective view of an embodiment of the device of the present invention in an expanded position.
Figure 2:
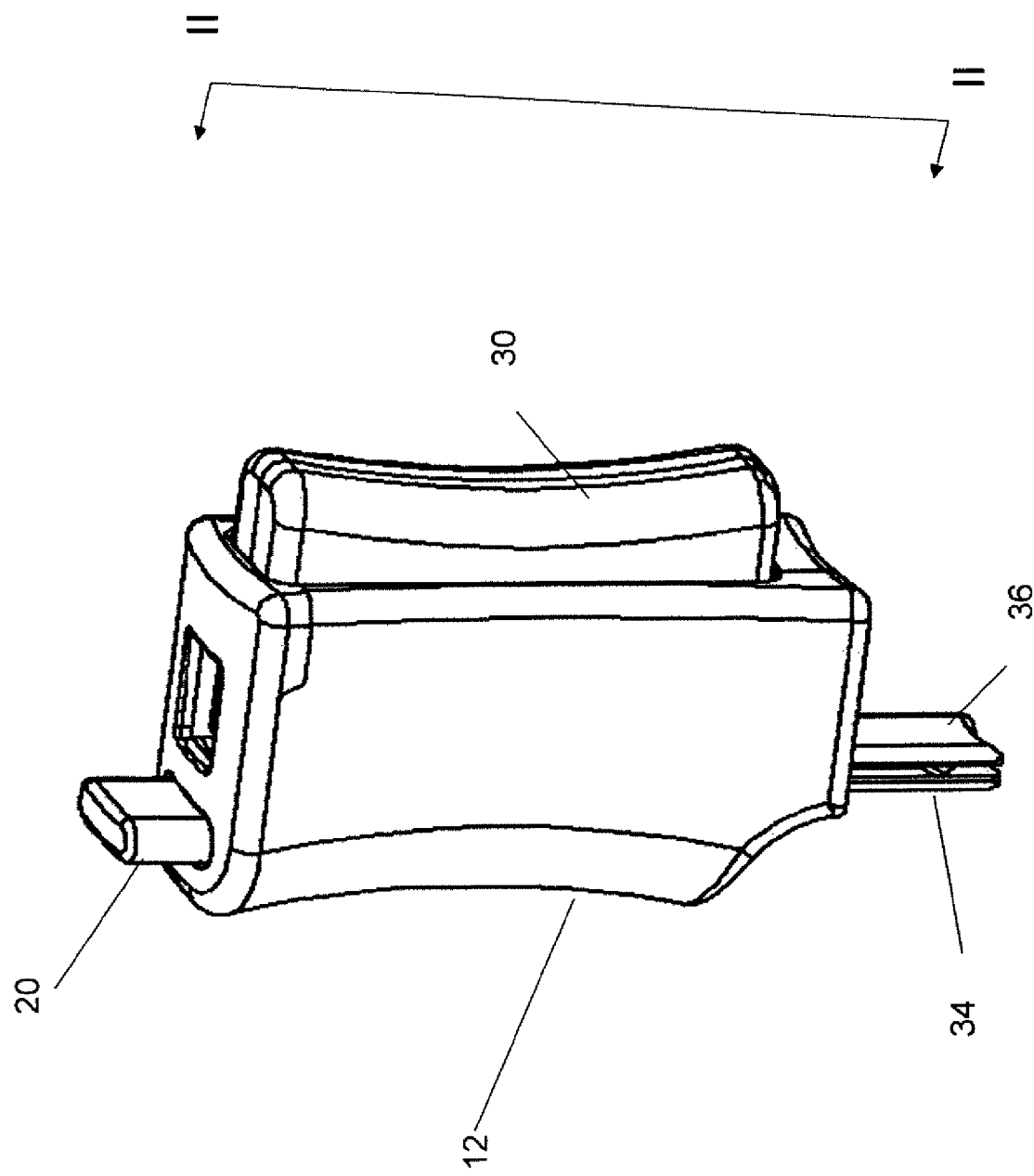
FIG. 2 is a perspective view of the device in a compressed position.
Figure 3:
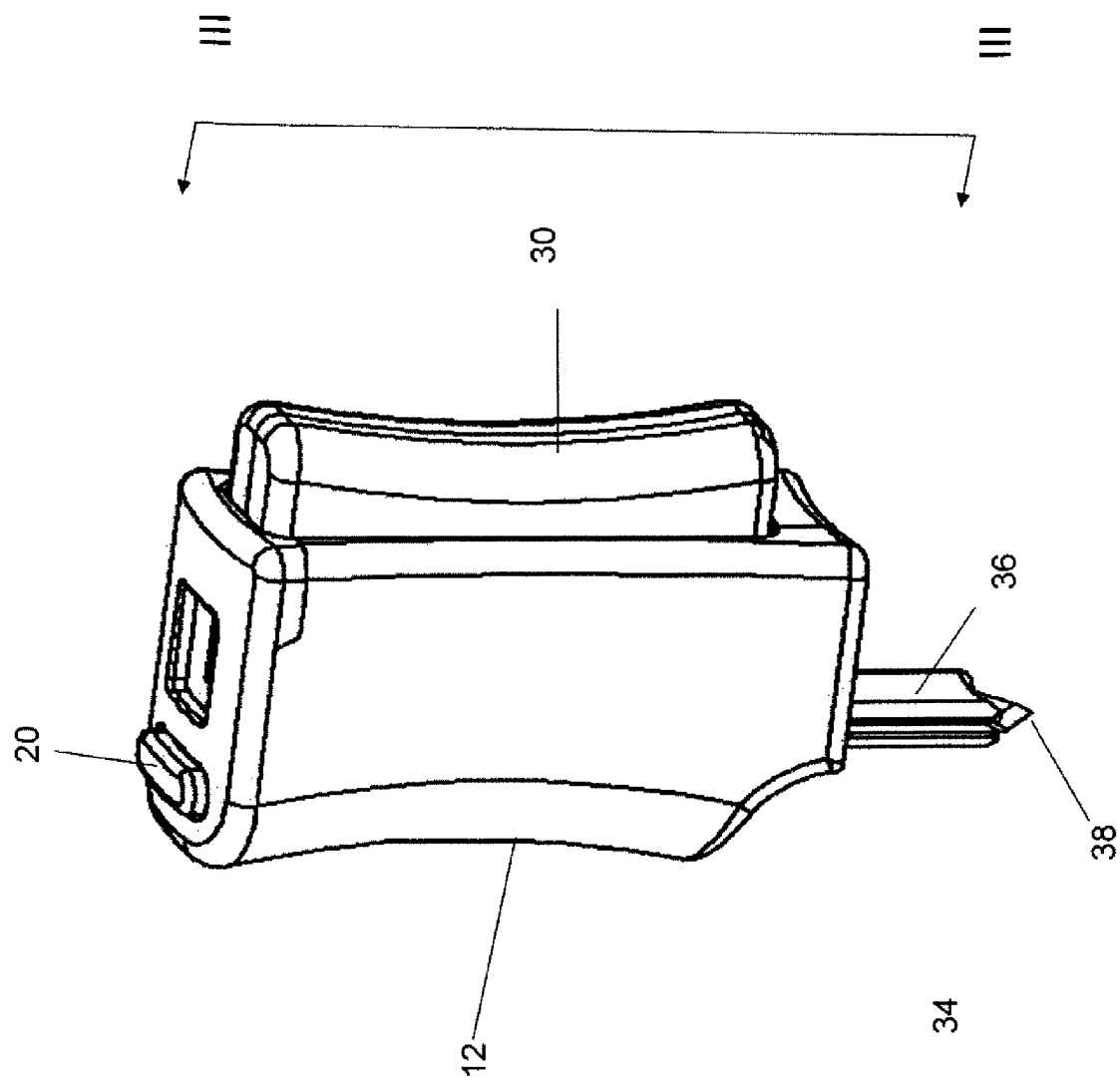
FIG. 3 is a perspective view of the device in a ready position with the blade exposed.

Referring to FIGS. 1-3, the cricothyroidotomy airway device 10 of the present invention allows emergency personnel to perform a cricothyroidotomy procedure faster and safer than conventional methods. The device has a retractable blade and an ergonomic grip. The device is spring loaded and angled to facilitate tracheal tube insertion. The device is intended to be used in emergency settings, on the scene of an accident or in an operating room.

The device undergoes three states when being used—expanded, compressed and blade exposed. The device in the expanded position is shown in FIG. 1, in the compressed position in FIG. 2 and with the blade exposed in FIG. 3.

Device 10 includes a two-part housing 12. Housing 12 acts as a foundation and support for each of the other components that make up the device. Housing 12 has an ergonomic shape to conform to the patient's neck and to fit comfortably within the user's hand. The housing includes three parts—sides 14A, 14B and cap 16. It should be appreciated that the housing can be split into three components for manufacturability and assembly. However, the housing can also be formed of any number of parts.

The device consists of numerous molded components, several stamped metal components, machined components, and springs. The materials can vary. For example, the molded components can be made of a suitable plastic, such as polyetheretherketon (PEEK)

Figure 4:
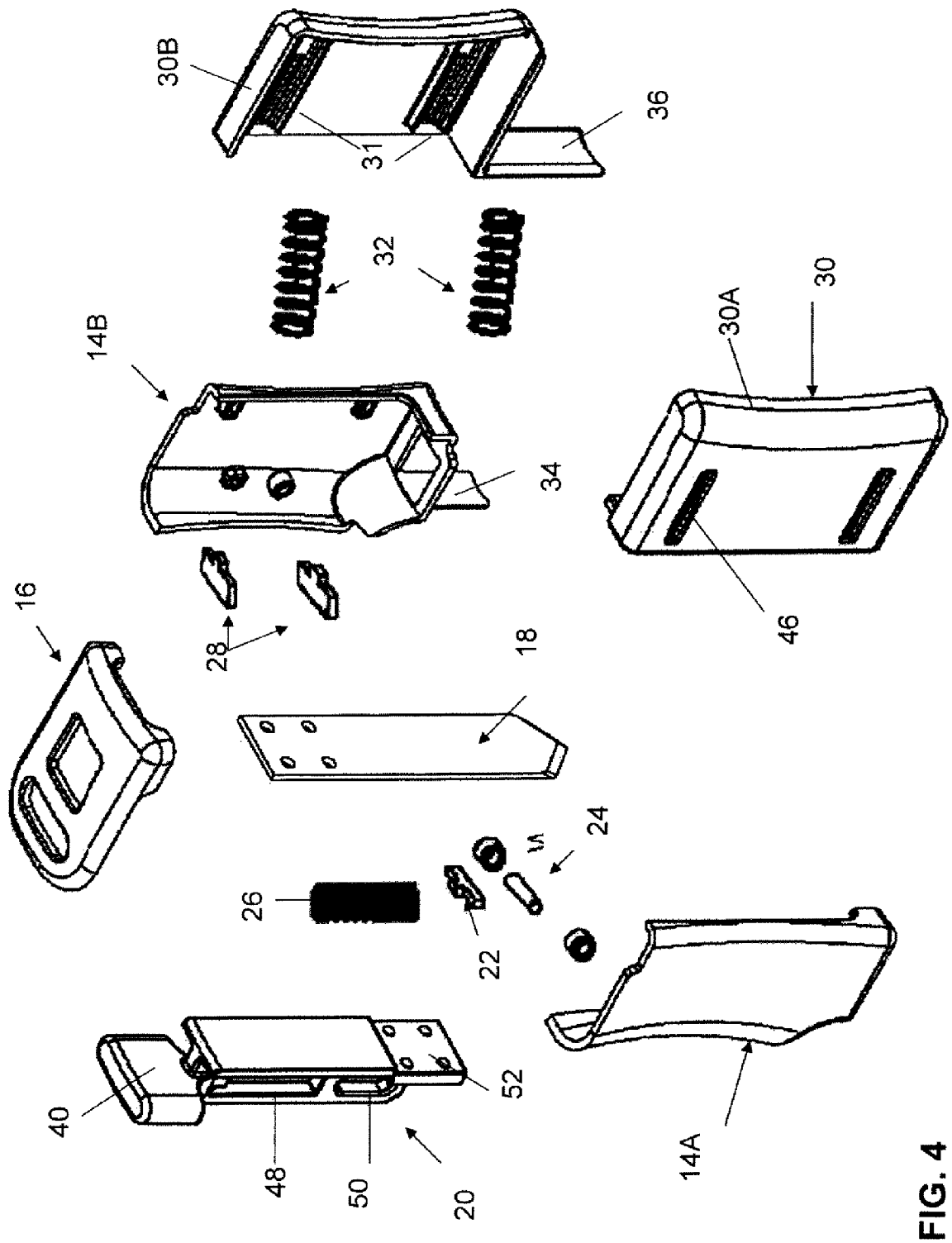
FIG. 4 is an exploded view of the components of the device of the present invention.

As shown in FIG. 4, sides 14A and 14b contain mating features that secure a blade 18, a blade actuator 20, blade actuator spring rail 22, blade actuator pin and washers 24, blade actuator spring 26 and palm grip rails 28, palm grip 30 and incision expansion springs 32, all of which are described further herein. Side 14B of housing 12 also includes a first prong 34. A second prong 36 is located on the bottom of palm grip section 30B. Prong 36 is movable in relation to prong 34 and together the two prongs act as a tissue separator and are used to form a blunt tip which aids the user to locate the cricothyroid membrane notch. The springs provide the driving force when spreading apart the incision made in the neck and through the cricothyroid membrane.

Figure 5A:
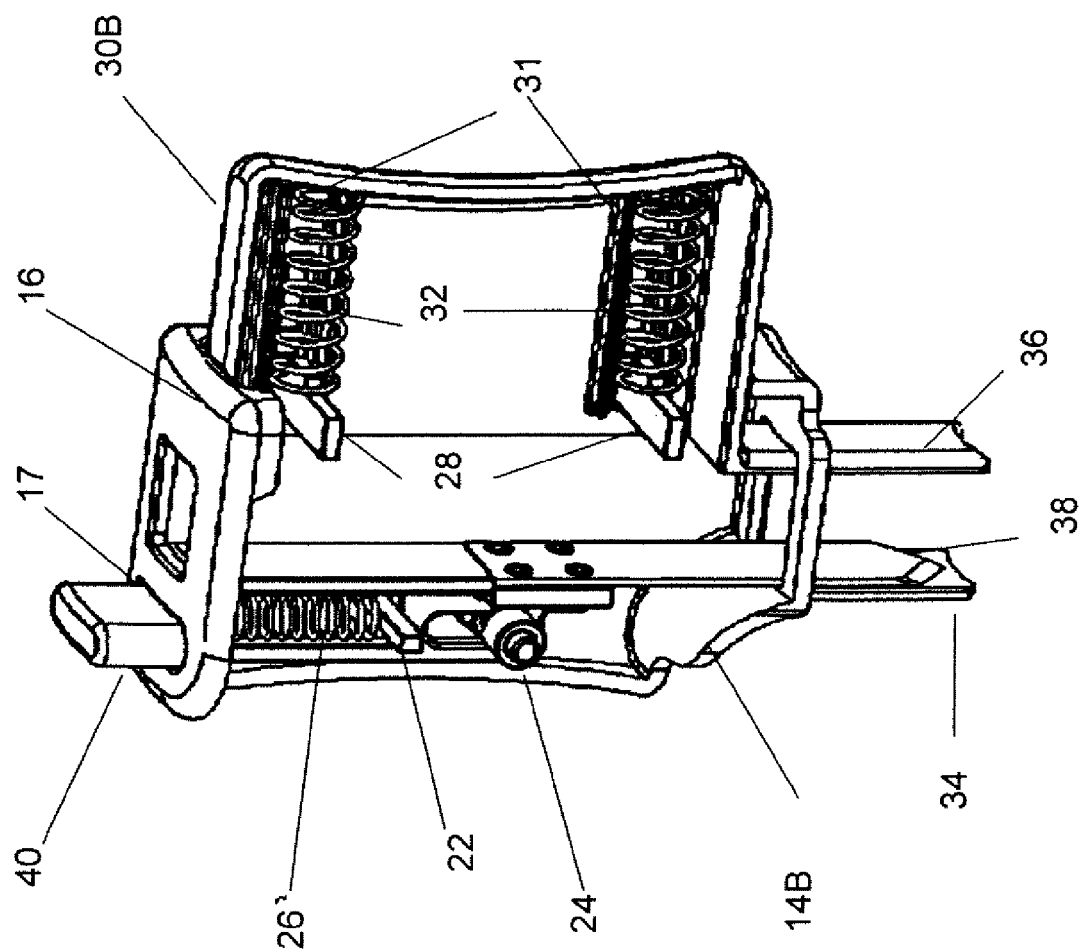
FIGS. 5A and 5B are cross-sectional views of the device taken along line I-I of FIG. 1.
Figure 5B:
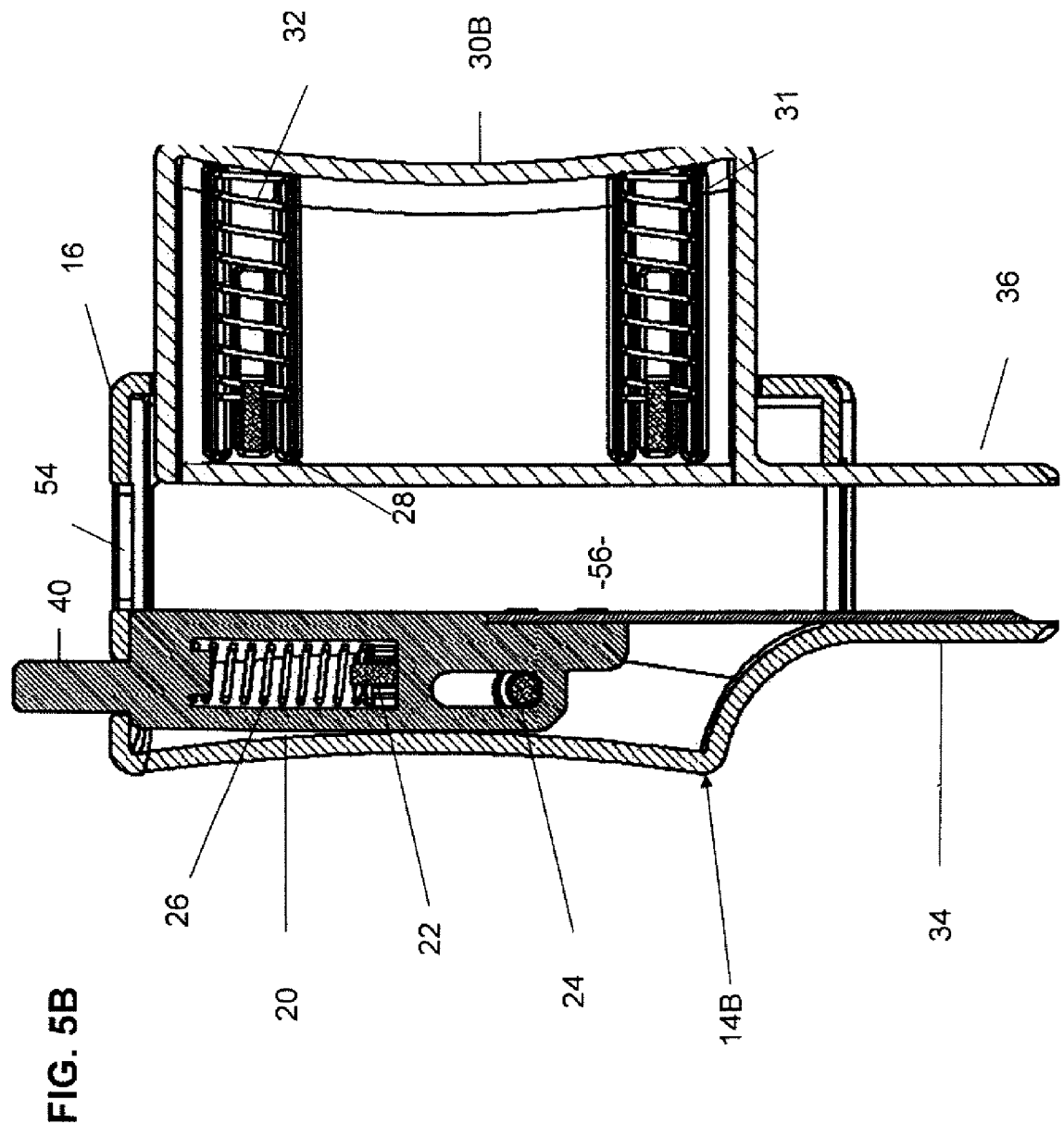

Palm grip 30 has two sections 30A and 30B. Each section 30A and 30B include a pair of palm grip tracks 31 that receive the incision expansion springs 32. Referring to FIGS. 5A and 5B, wherein only one side of the device is shown, palm grip 30 is movably disposed within housing 12. The opposed ends of palm grip rails 28 are located in notches 42A, B in housing sides 14A and 14B, shown in FIGS. 6A and 6B.

Figure 7A:
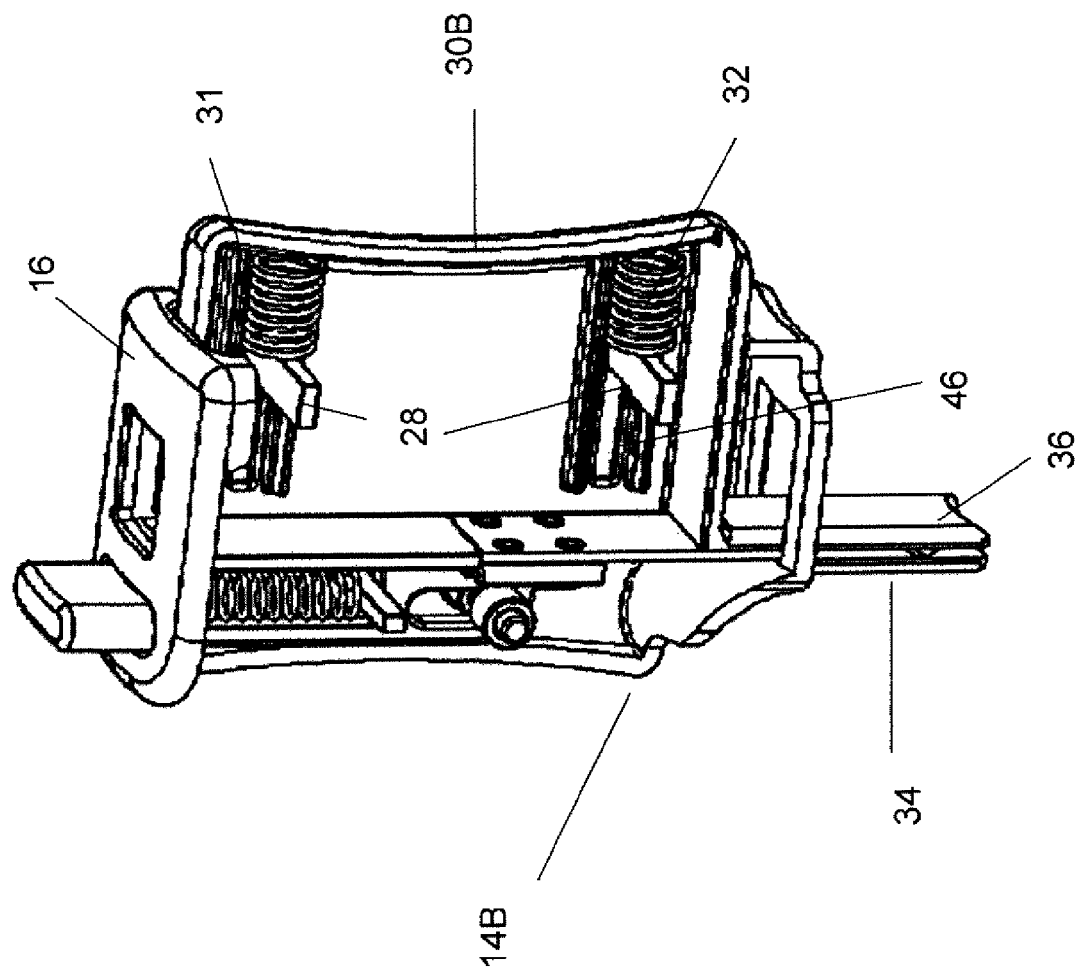
FIGS. 7A and 7B are cross-sectional views of the device taken along line II-II of FIG. 2.
Figure 7B:
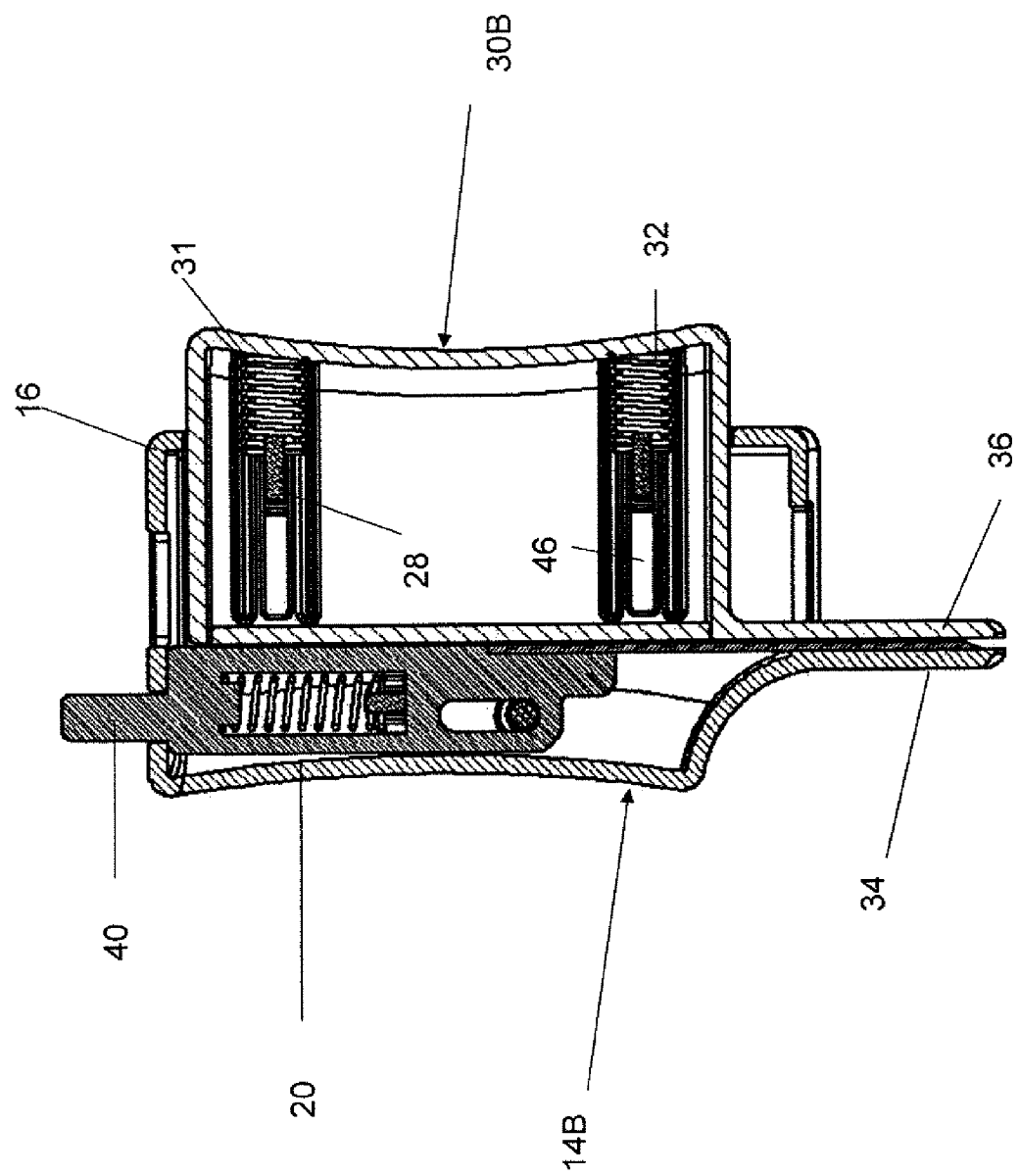

Each end of rails 28 extend through slots 46 located within tracks 31. Palm grip rails 28 are designed to provide a positive stop for palm grip's 30 range of linear motion, as well as to capture one end of the incision expansion spring 32. As shown in FIGS. 2 and 7A-7B, as grip 30 is moved inward, grip 30 moves along rails 28 that extend trough slots 46 of tracks 31 to compress springs 32. Simultaneously, prong 36 is moved adjacent prong 34 to sandwich tip 38 of blade 18 therebetween. At this position the device is in the compressed state.

Once the device is in the compressed position, the blade can be released. Referring to FIG. 4 again, blade actuator 20 includes a first aperture 48 and a second aperture 50. A button 40 is located at one end and a blade fastening portion 52 is located on the opposed end. As shown in FIGS. 5A and 5B, when the blade in an unreleased state, button 40 extends through an opening 17 in cap 16.

Blade actuator pin 24 mates with aperture 50 in blade actuator 20. A washer is placed on blade actuator pin 24 on either side of the blade actuator to keep the actuator properly oriented within the housing. Blade actuator spring 26 is located within aperture 48. Blade actuator spring rail 22 is located within aperture 48 and communicates with one end of spring 26. Each end of rail 22 is held in notch 44A, B (FIGS. 6A and B) of the housing sides 14A, B. The palm grip rails 28, blade actuator spring rail 22, and blade actuator pin 24 all provide support to the assembled housing by improving its compressive resistance force.

Figure 8A:
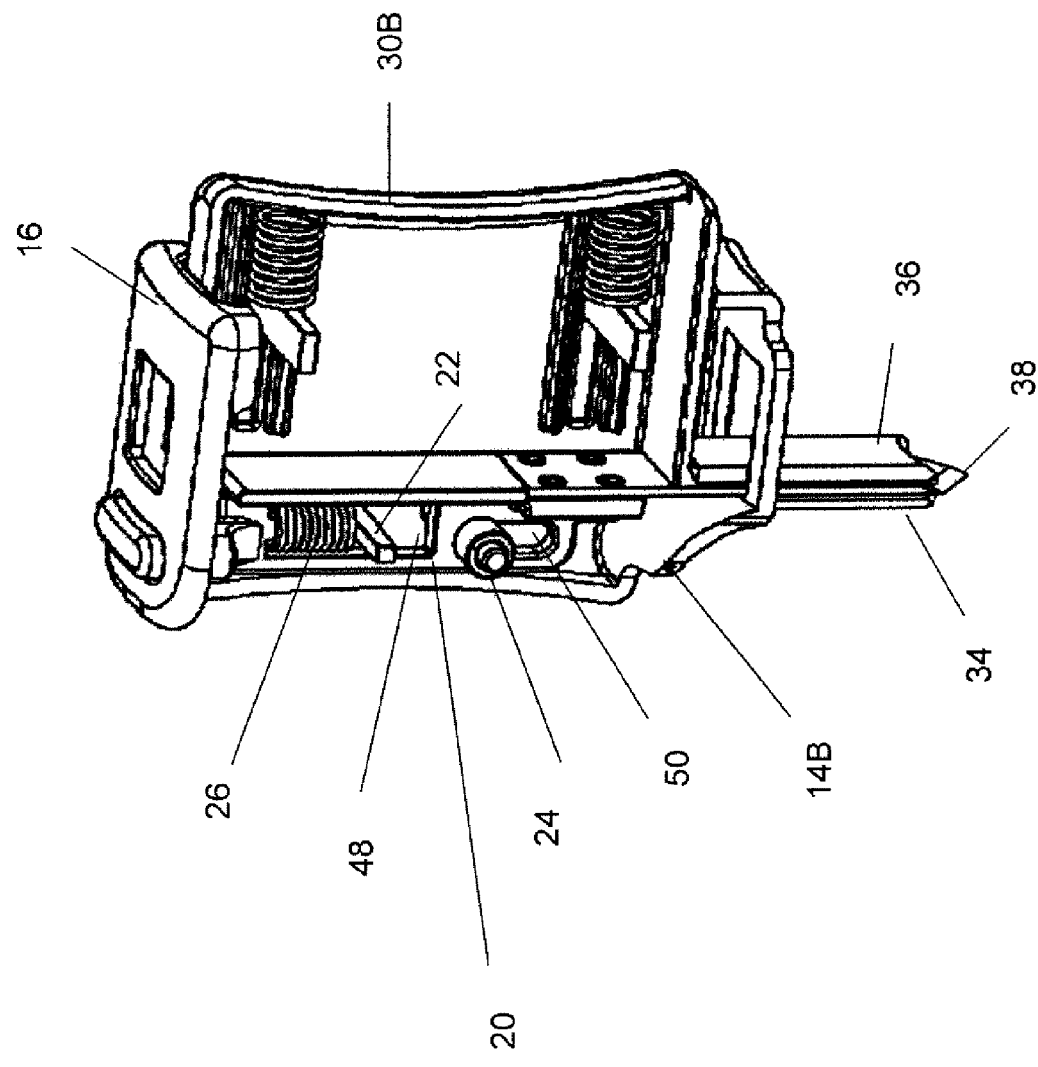
FIGS. 8A and 8B are cross-sectional views of the device taken along line III-III of FIG. 3.
Figure 8B:
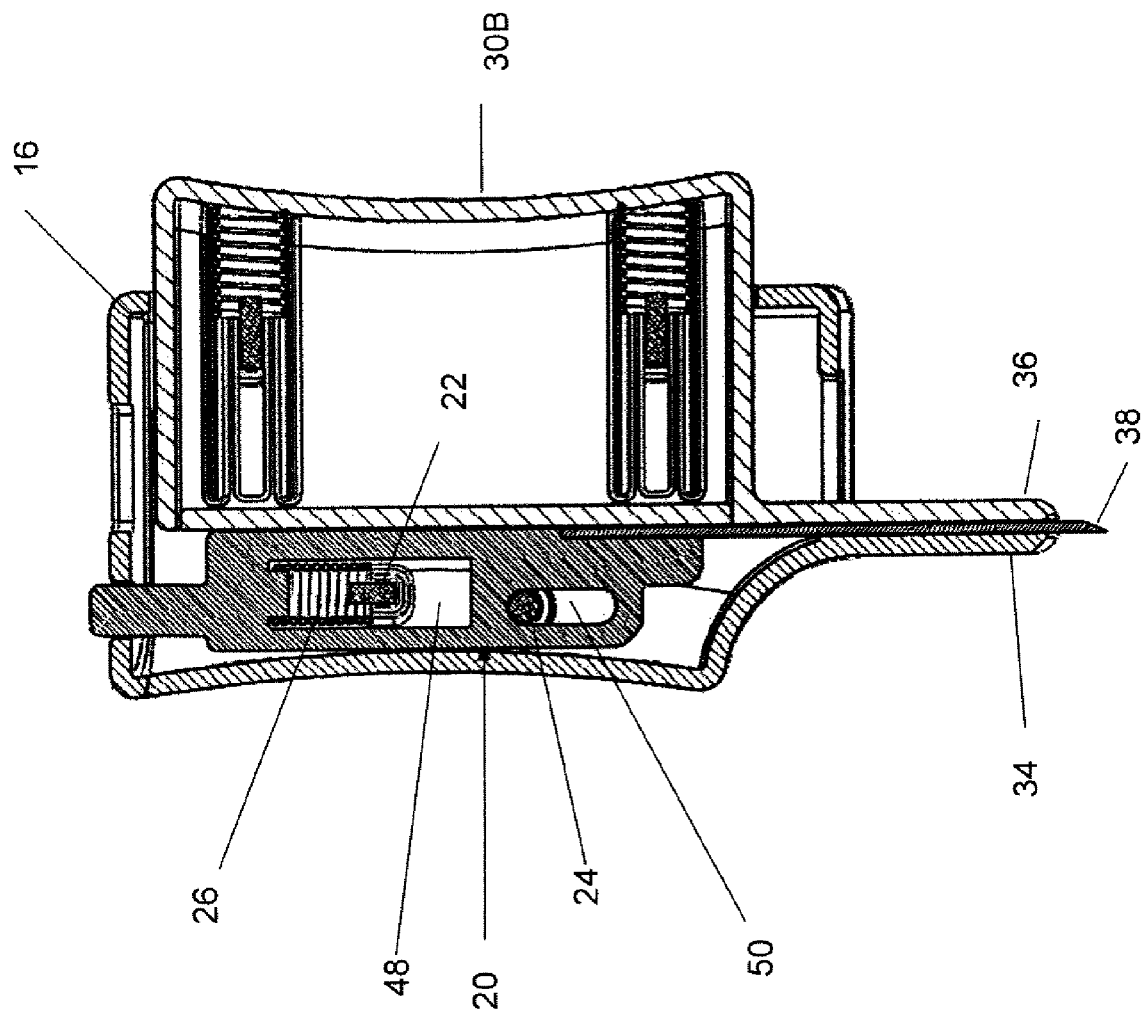
Figure 9:
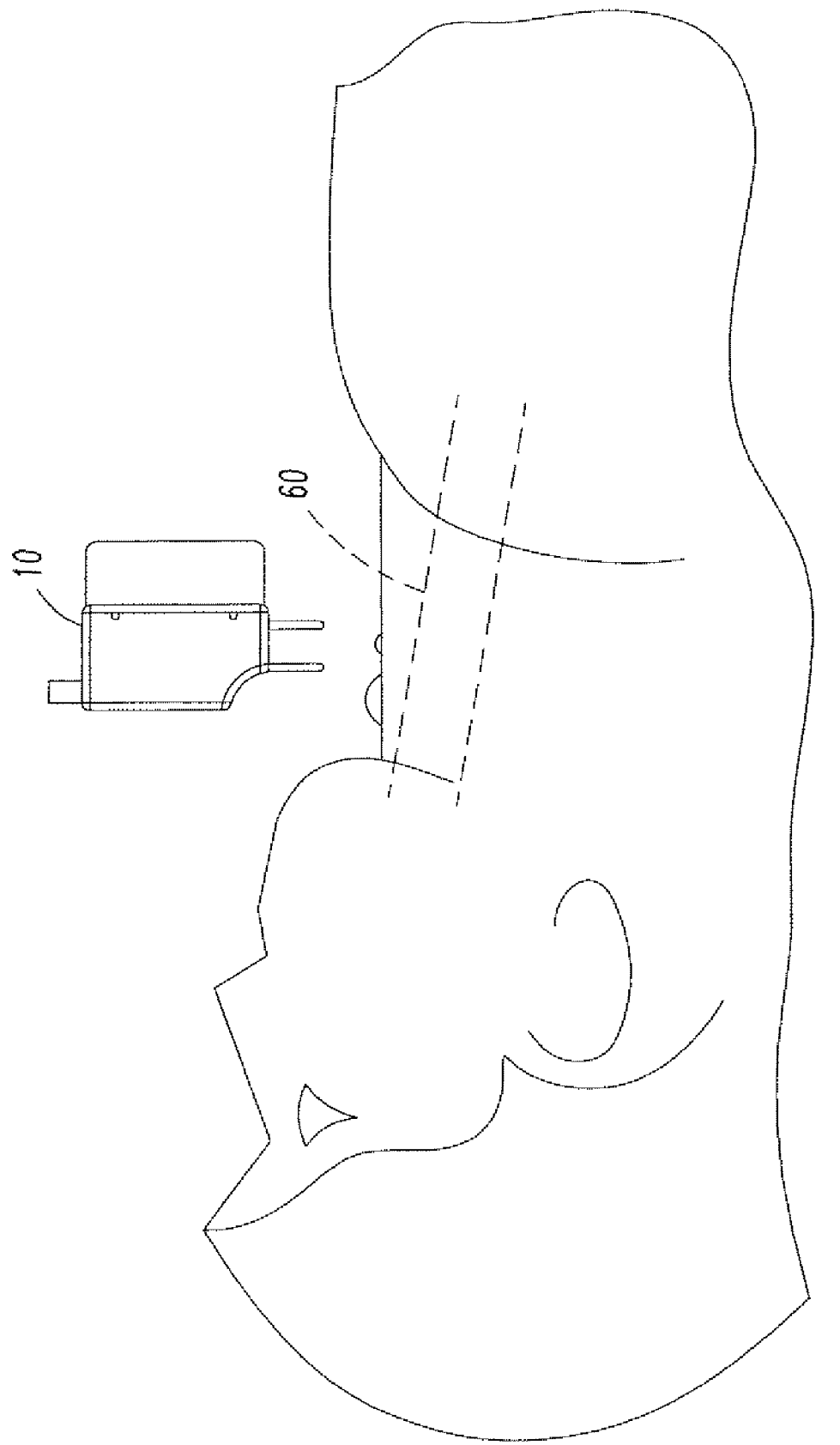
FIGS. 9-17 illustrate the use of the device.

Referring to FIGS. 8A and 8B, blade actuator 20 acts as a linkage between the user's thumb and blade 18. When button 40 is pressed or released blade actuator 20 is guided up and down within housing 12. Blade 18 is fastened to the lower recessed portion 50 of the blade actuator. When button 40 is pressed downward, spring 26 is compressed by rail 22 as it moves within aperture 48. Simultaneously, pin 24 moves within aperture 50 until it abuts against the end of the slot. Tip 38 of blade 18 extends outward from prongs 34, 36.

The primary function of the blade is to puncture through the cricothyroid membrane enough to adequately be able to insert the tissue separator prongs 34, 36. As will be described further herein, incision expansion springs 32 are designed to be weak enough to compress with normal hand strength yet strong enough provide adequate force to keep the prongs separated and the incision open. The blade actuator spring is designed to provide an upward force on the blade actuator, which in return keeps the blade retracted safely within the device's housing.

Figure 10:
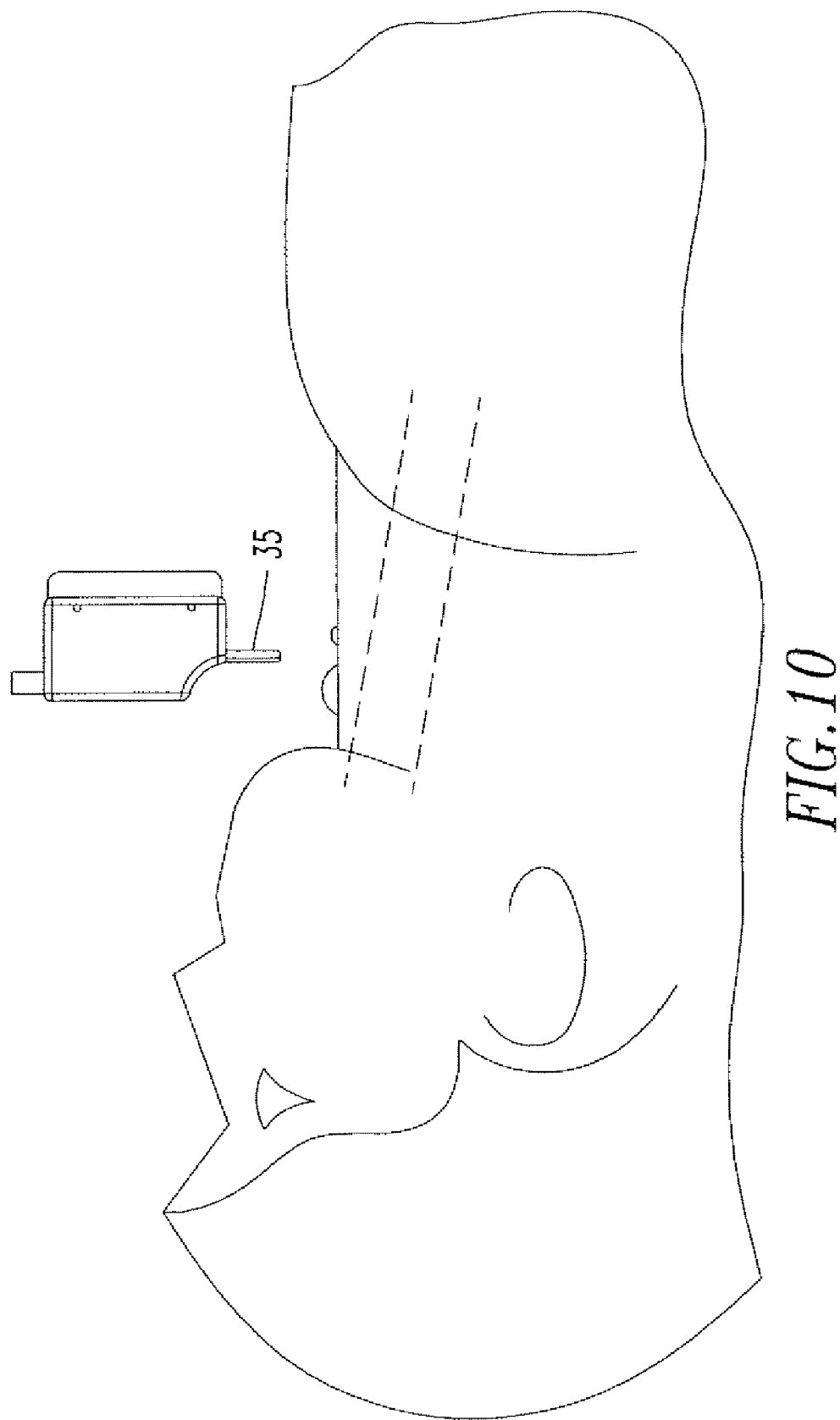
Figure 11:
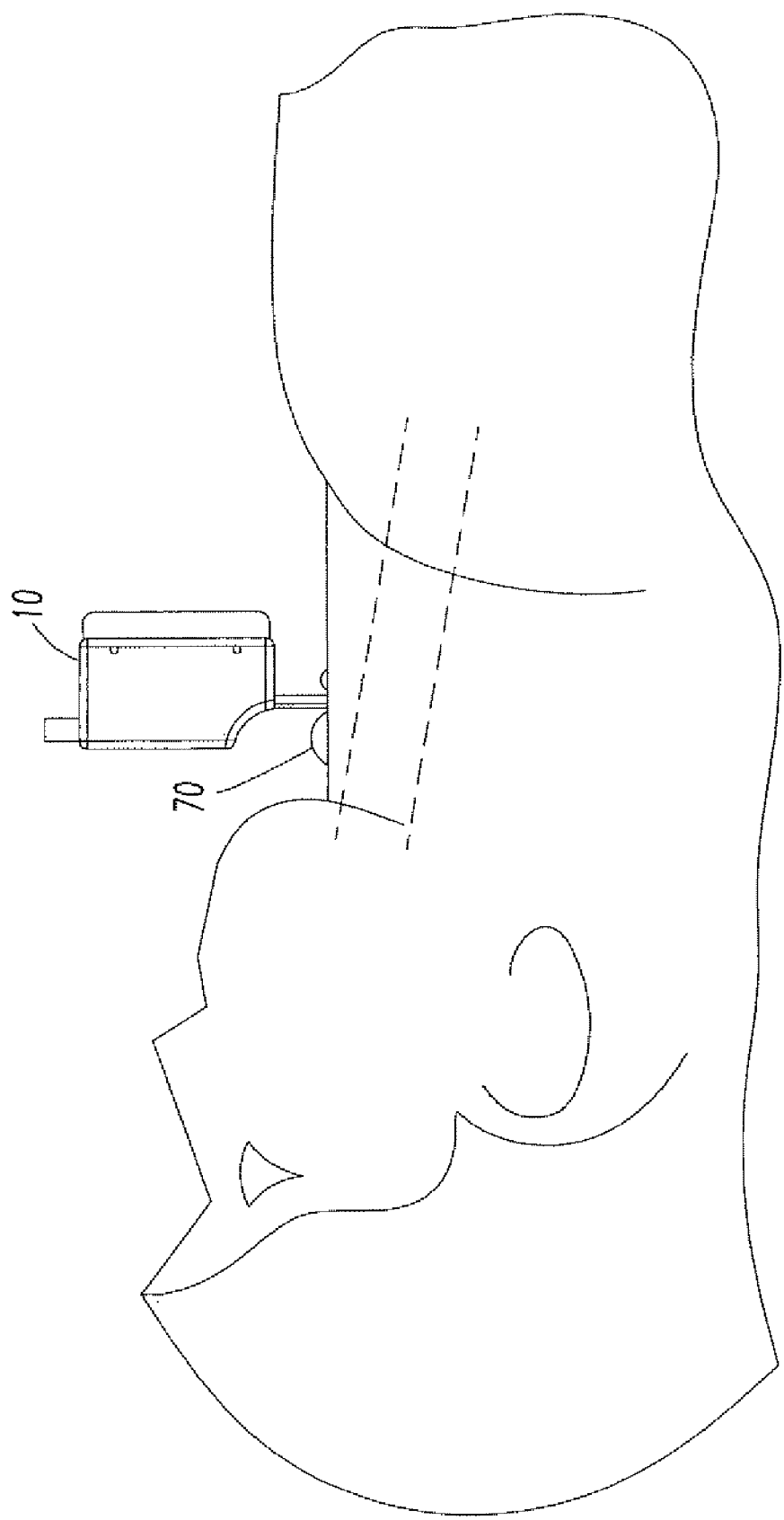
Figure 12:
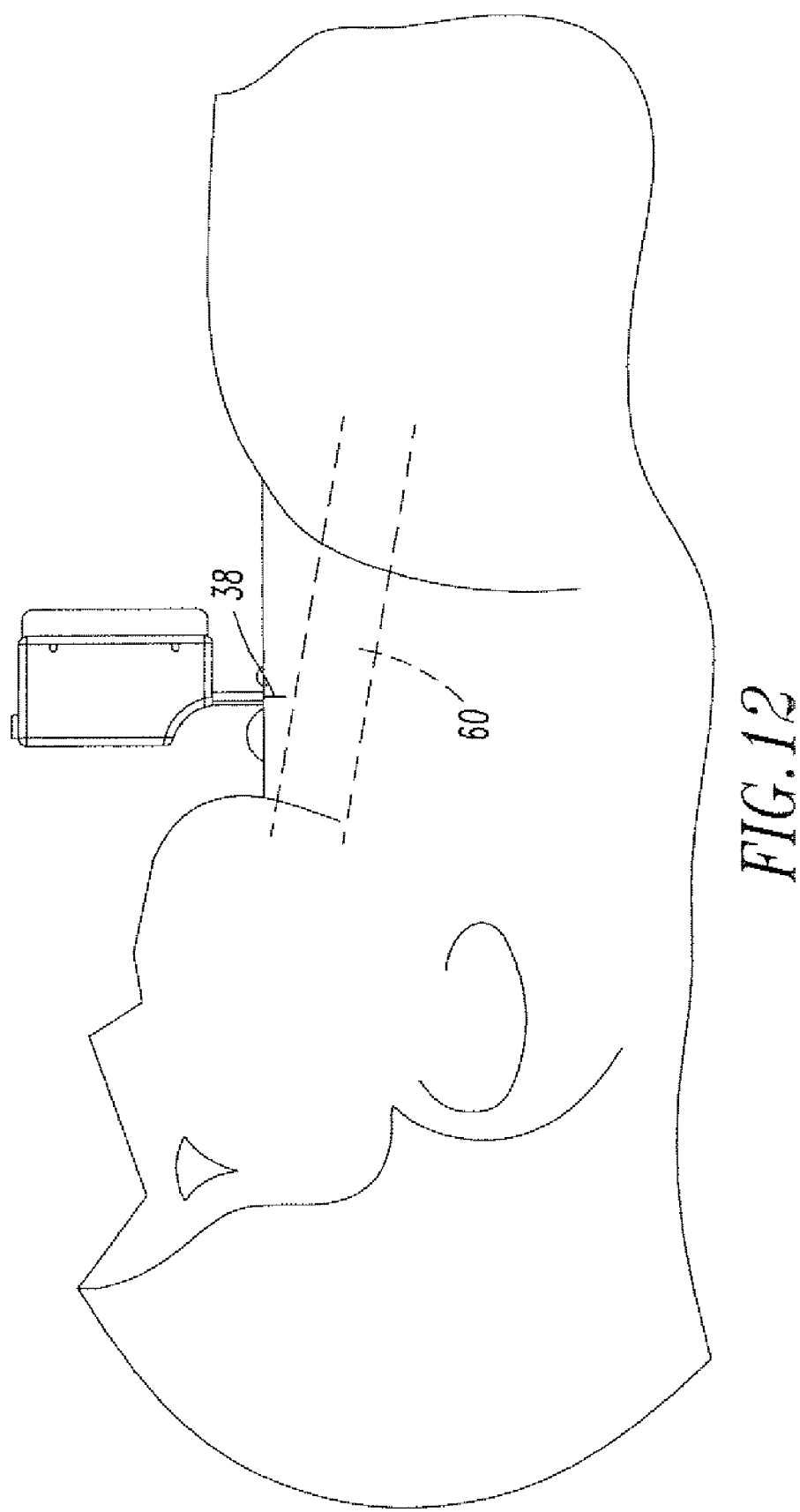
Figure 13:
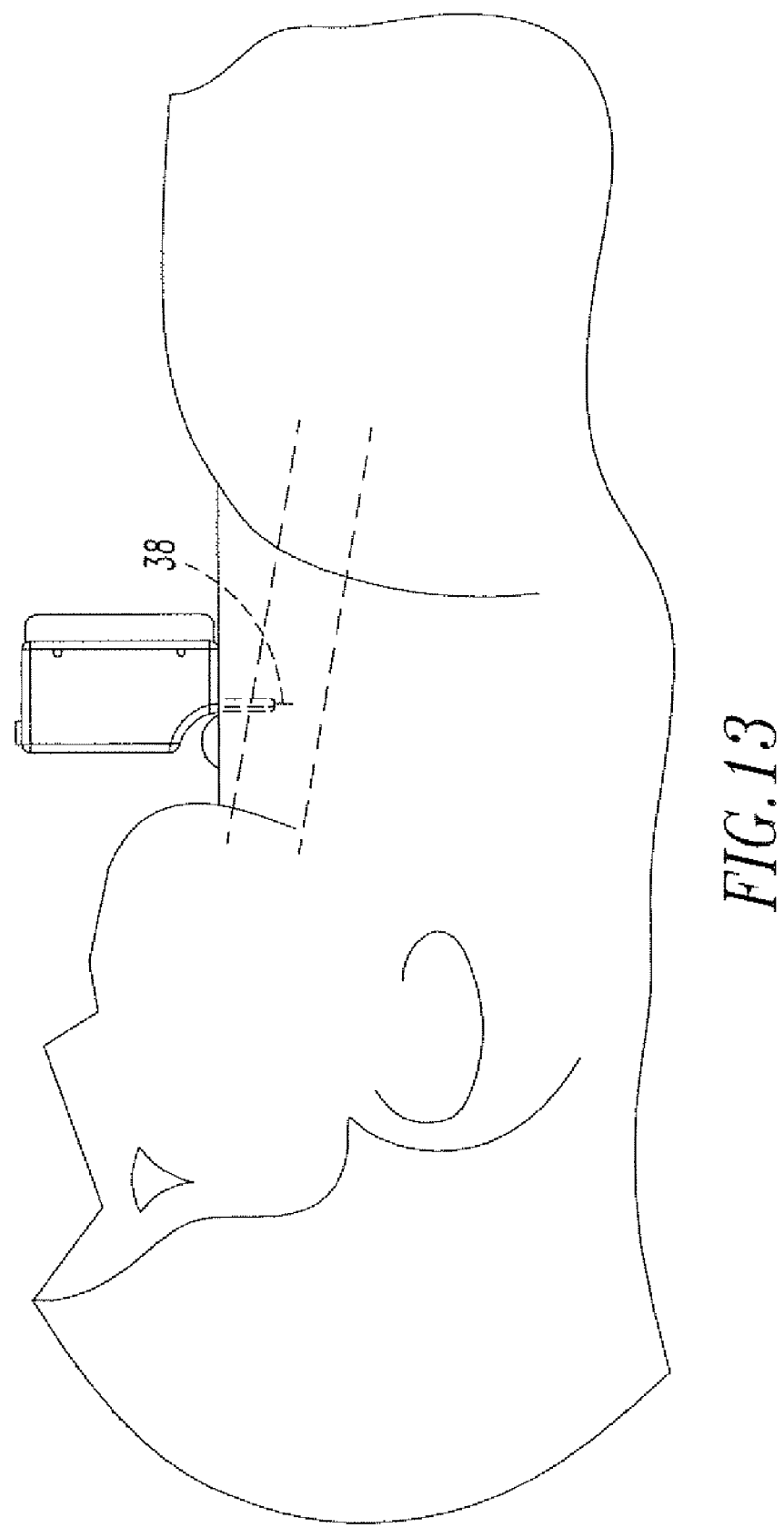

Cap 16 has an opening 54 to receive a tracheal tube. As will be described further herein, the tube is inserted through opening 54 and down through passage 56 in the device until it exits through separated prongs 34, 36. See FIGS. 1 and 5B Referring to FIGS. 9-17, in order to create an emergency airway, first the device user must locate a point of entry. The device of the present invention is designed to enter through the cricothyroid membrane 60 via percutaneous insertion while the patient is lying on their back. As shown in FIG. 10, when the user compresses the device between their fingers and palm, the two tissue separators come together to form a blunt tip 35. The user can then use the blunt tip to probe the neck area, as shown in FIG. 11, until it lands below the thyroid cartilage and directly above the cricothyroid membrane. When in place, the user advances the retractable blade through the skin and cricothyroid membrane, as shown in FIGS. 12 and 13.

Figure 14:
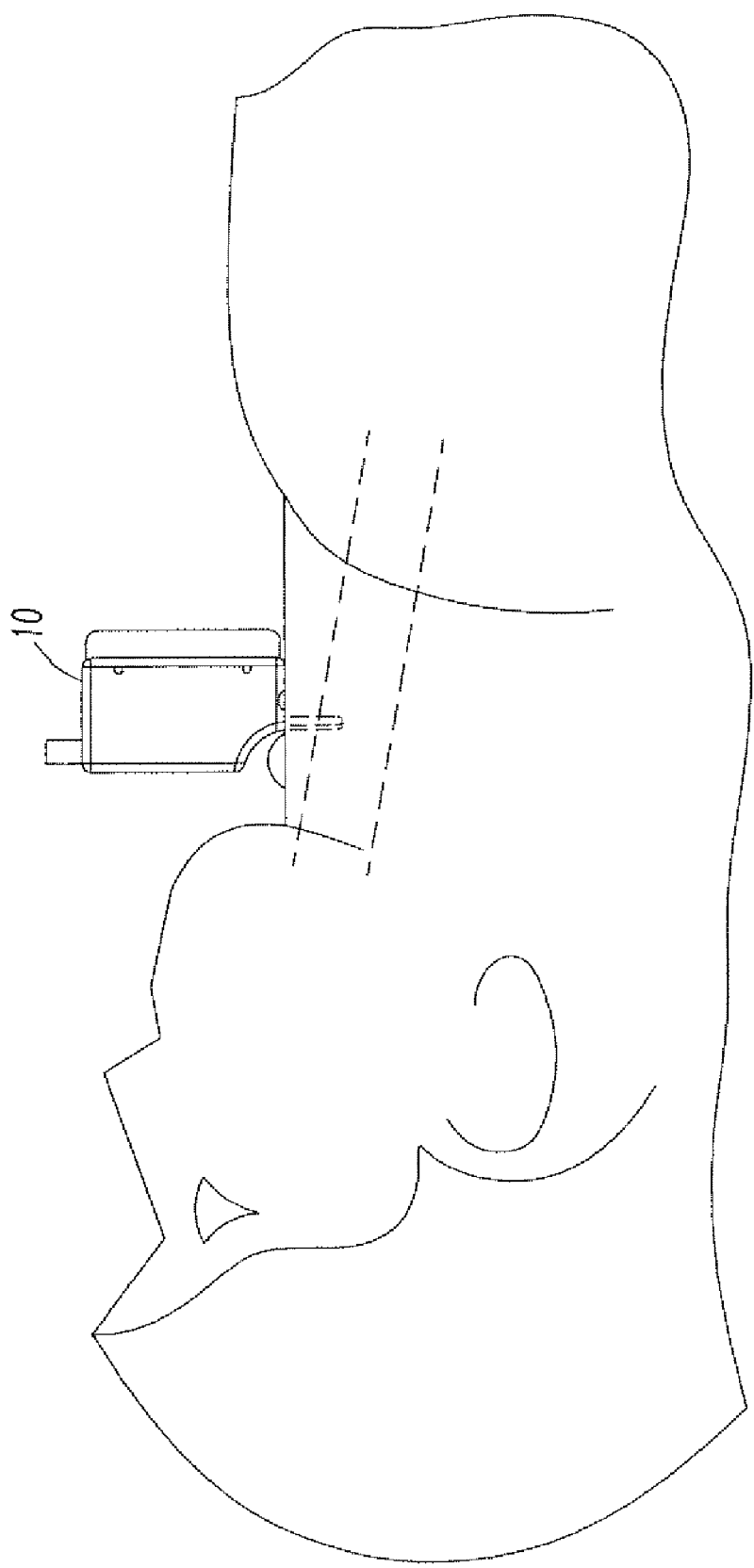
Figure 15:
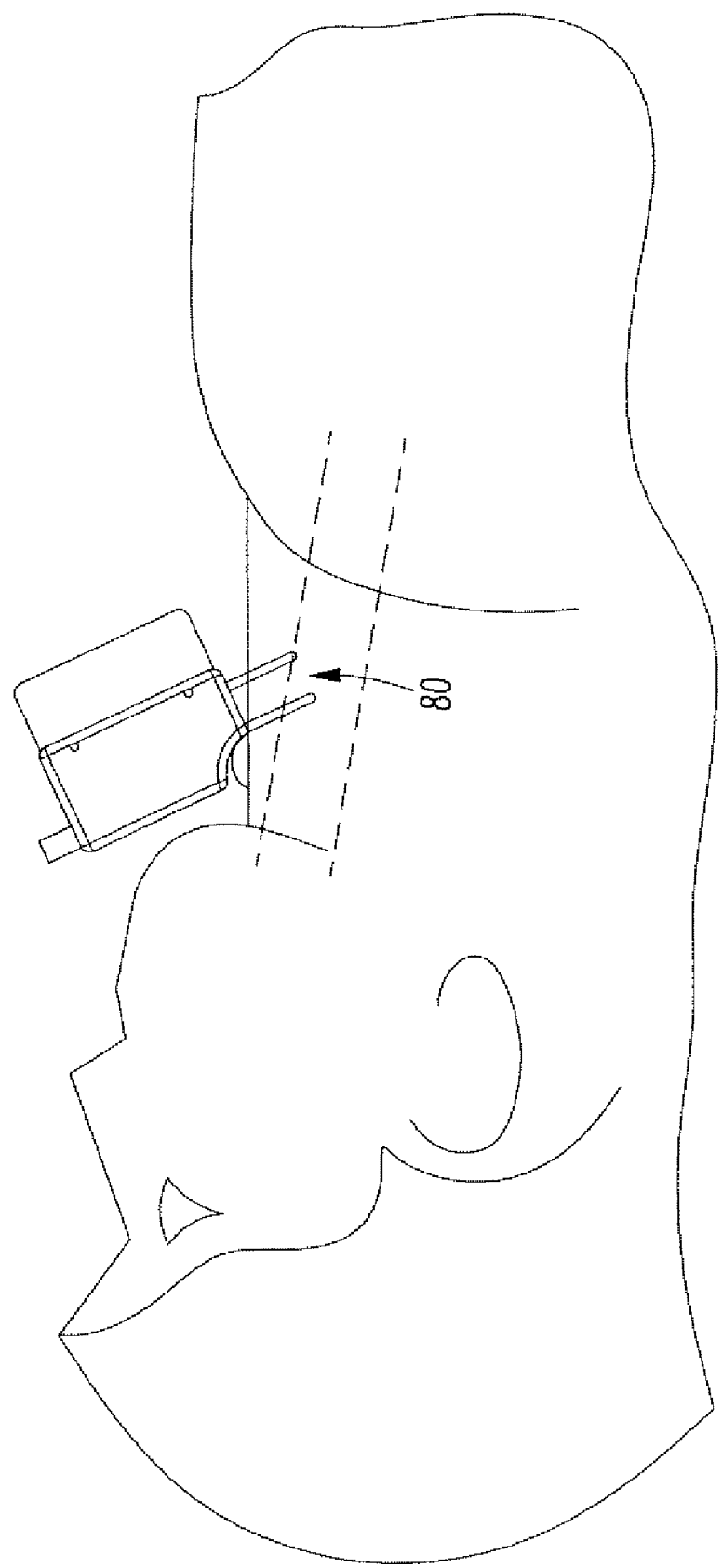
Figure 16:
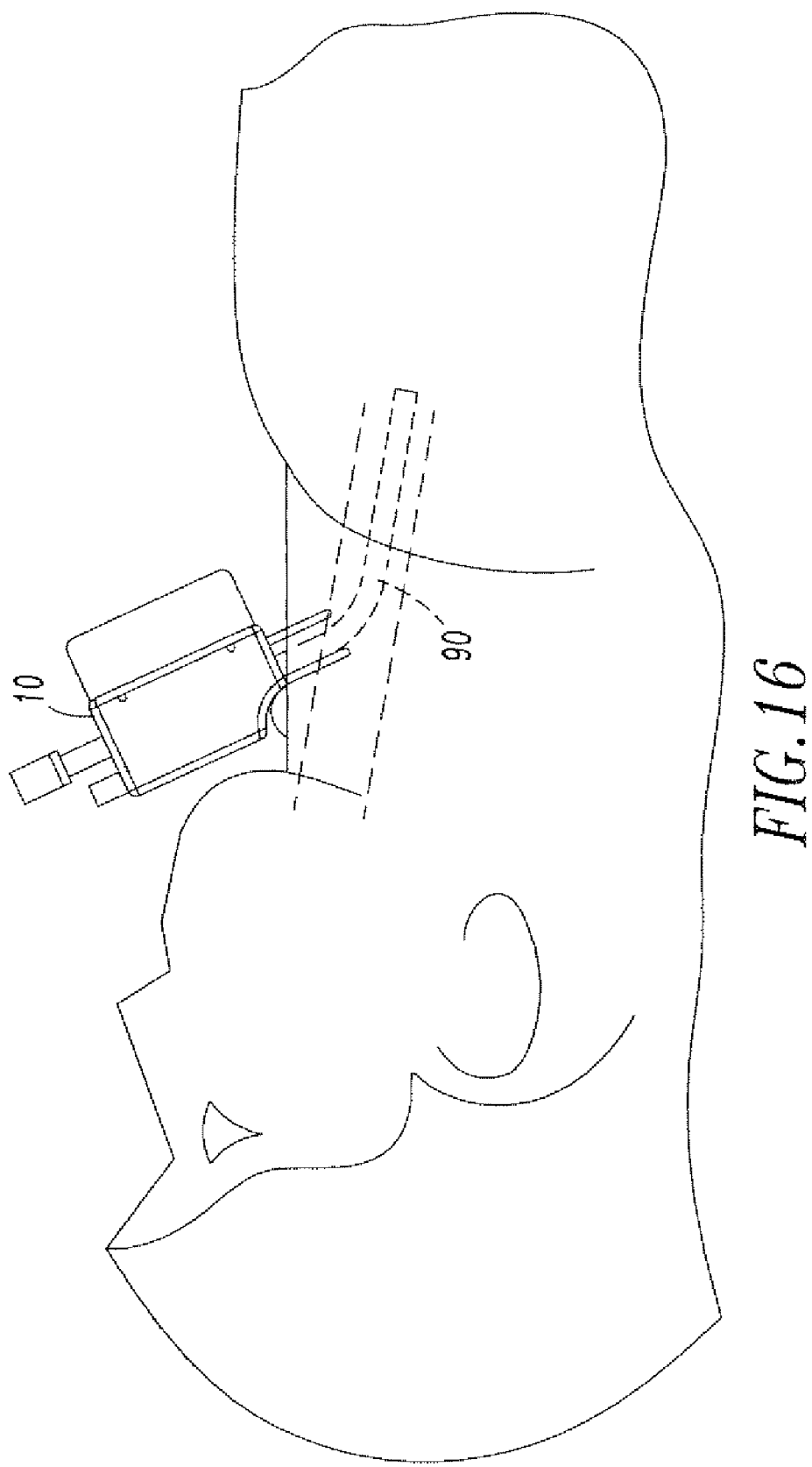
Figure 17:
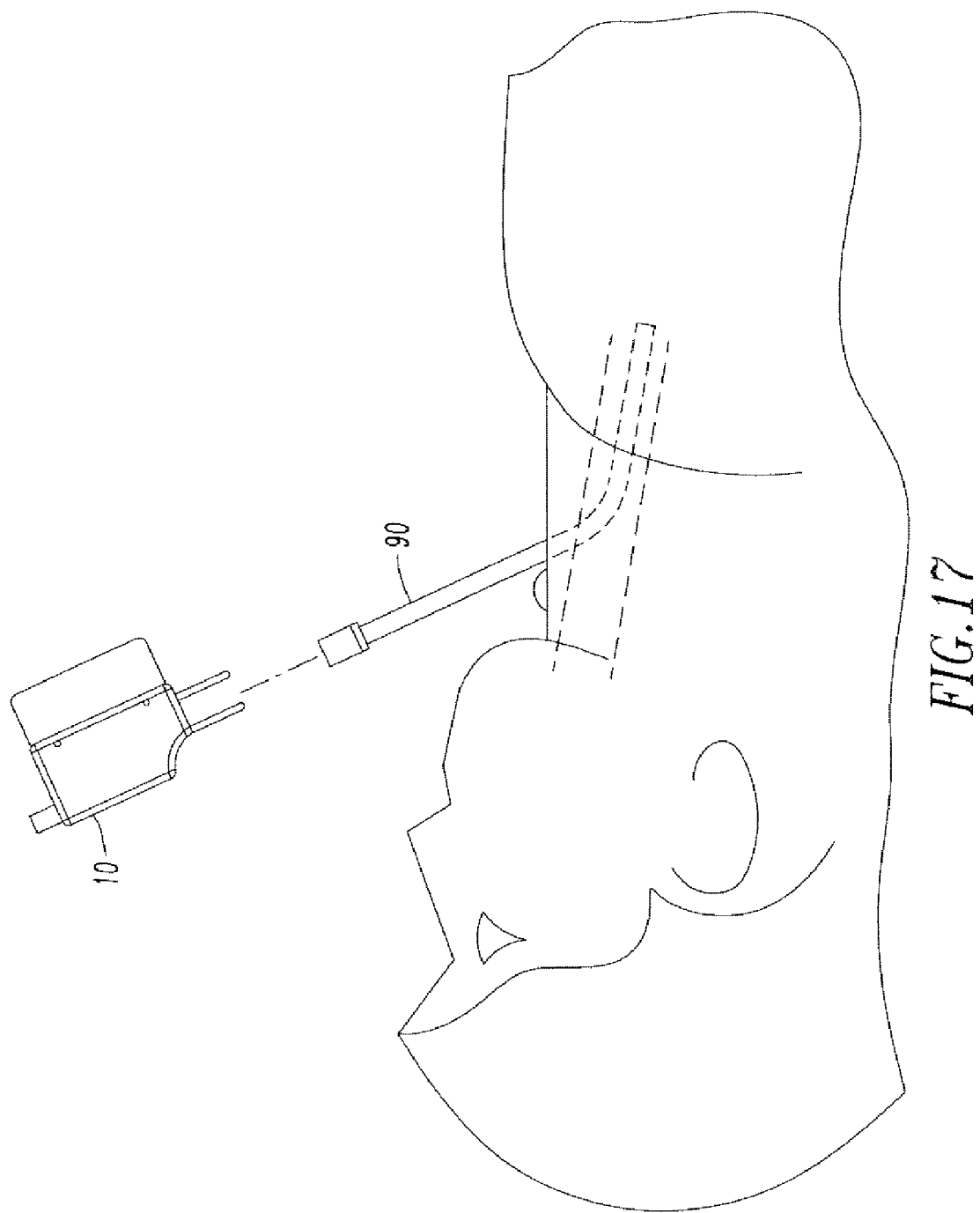

The user may then retract the blade and insert the tissue separators through the newly formed incision, FIG. 14. Once the device has bottomed out on the skin of the neck, the user releases their grip on the device, causing the tissue separators to expand and instantly create an airway as shown in FIG. 15. The user then rotates the device towards the face. This angles the tissue separators and allows a tracheal tube 90 to be inserted down towards the lungs. See FIG. 16. Once the tube 90 is inserted to the appropriate depth, the device can be removed by sliding it out of the incision and over the proximal end of the tracheal tube, as shown in FIG. 17.

The device is designed to be compatible with an array of standard endotracheal tubes, for example, a 7.3 mm outer diameter oral/nasal tube with a 5.5 mm inner diameter. This design feature allows the paramedic to feel more comfortable while performing the procedure because there is a level of familiarity with their existing tracheal tubes.

Referring to FIGS. 18-24, a second embodiment of the device of the present invention will be described. As with the previous embodiment, the device allows emergency personnel to perform a cricothyroidotomy procedure faster and safer than conventional methods. The device is designed to be compatible with an array of standard endotracheal tubes. There is a quick release mechanism incorporated into the device to allow for easy insertion and removal of the endotracheal tube. The device also is designed to allow the implementer to easily locate the cricothyroid membrane by referencing off of the thyroid gland. The base plate of the device is cut away so when implemented, the thyroid gland has an area to reside. The device is designed so when compressed, allows for percutaneous entry. The "needle" action is comprised of two pieces that are pulled apart once the device is released. The pulling motion spreads the incision open, creating a gap or hole into the trachea. The needle geometry is designed to grip onto the inner trachea wall and remain in place until the trachea tube is inserted through the newly formed hole. A spring loaded button mechanism grips the tube in place by a compressive force. The invention is intended to be used in emergency settings, on the scene of an accident or in an operating room.

Figure 18:
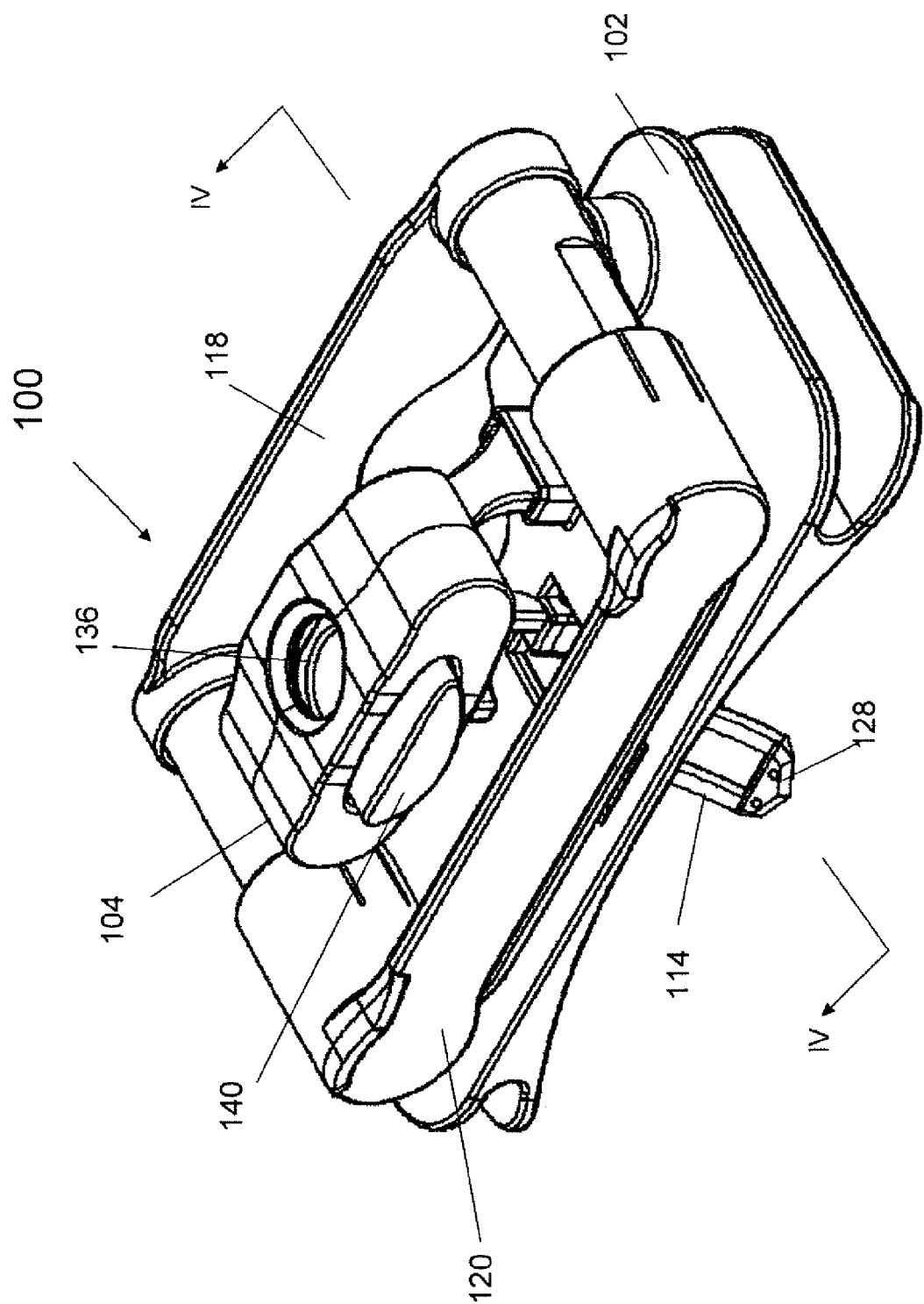
FIG. 18 is a perspective view of another embodiment of the device of the present invention in an expanded position.

Device 100 has two main states, released and compressed. Initially the device comes released, as shown in FIG. 18, and is compressed upon entry into the cricothyroid membrane, see FIG. 23.

Figure 19:
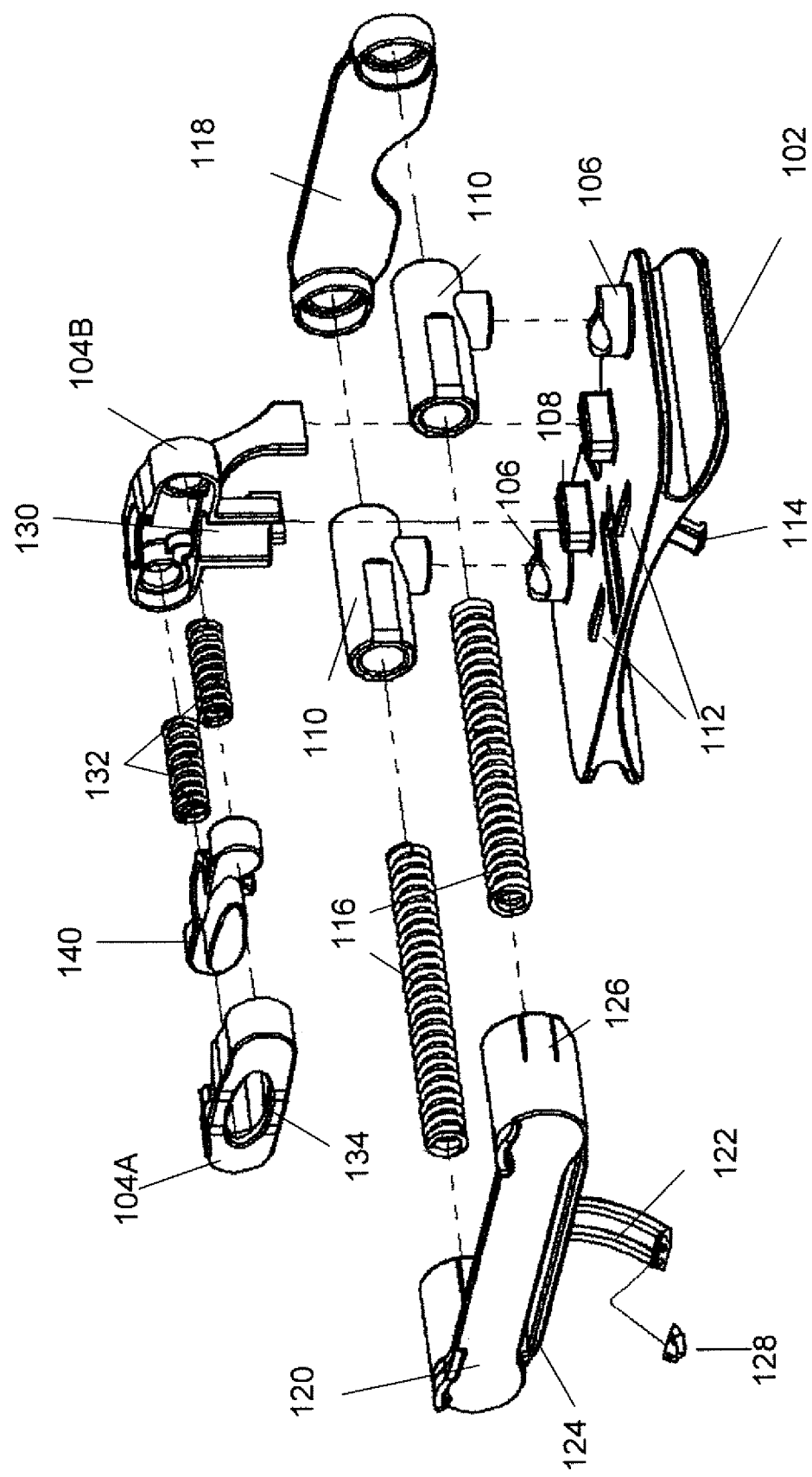
FIG. 19 is an exploded view of the components of the device.

Referring to FIG. 19, device 100 includes a base 102. Base 102 acts as a foundation and support for the each of the other components that make up the device. The base's shape is curved and designed to conform to the patient's neck. Mating features 106, 108 are included on the top of the base to locate spring housings 110 and a clamp housing 104. A prong 114 is attached to the bottom side of base 102 which acts as one of two features that separate the cricothyroid membrane and allow for tracheal insertion. Prong 114 is hollow to allow another prong to be received therein. Prong 114 also is chamfered on one edge and tapered slightly allowing for easy insertion. Prong 114 also has ledges that catch directly on the cricothyroid membrane when inserted, preventing removal until the device is in its compressed position. The prong also is shaped like a curve to direct the endotracheal tube down towards the patient's lungs. Protrusions 112 are located on top of base 102 to keep the device in the released position.

Spring housings 110 are positioned to base 102 via mating features 106. A proximal push plate 120, which will be described further herein, is attached to one end of spring housings 110. When these pieces are assembled they form a distal housing for return springs 116. A distal support plate 118 attaches to the other end of spring housings 110. Return springs 116 are selected so that they are light enough to be compressed manually, while strong enough to provide adequate force to open the incision.

Distal support plate 118 acts as a location for the user's fingertips when compressing the device, prior to insertion into the neck. It also provides a distal wall for the return spring housing. The distal support plate is shaped to accommodate the thyroid gland, which commonly is referred to as the Adam's apple.

Proximal push plate 120 slides over both spring housings 110 and is proximally restricted by a slightly flexible snap feature 126 located at several locations, providing the proximal wall to the return spring housing. Features 126 deflect around spring housings 110 to enable housings 110 to pass therethrough, but to prevent the push plate from extending beyond, thus defining the motion boundaries of the device.

A prong 122 is attached to the bottom side of proximal push plate 120, which acts as the other feature that separates the cricothyroid membrane and allows for tracheal insertion. Prong 122 has a feature that once inserted, cannot be removed until the device is in its compressed position. The prong also is shaped like a curve to direct the endotracheal tube down towards the patient's lungs. The center of the prong is hollowed out so that prong 114 attached to base 102 can slide within it when the device is in its compressed position. The front side of proximal push plate 120 is solid to provide a location for the user's thumbs when compressing the device. A support 124 is strung along the bottom to mate with the raised features on the base of the device and to proved vertical support.

As described above clamping housing 104 attaches to base 102. Housing 104 has a proximal 104A and distal 104B clamping housing section. Distal clamp housing section 104B has a guide 130 to guide the tracheal tube down into the incision and elevate the endotracheal clamp so that the proximal push plate can reside under when the device is in its compressed position. The distal clamp housing 104B also provides a distal support for clamp springs 132 and has features that mate and align it with proximal clamp housing 104A. Section 104B also acts as a guide for a button 140 when it is actuated. Clamp springs 132 are selected so that they are light enough to be compressed manually while strong enough to provide adequate force to keep the endotracheal tube in place.

Proximal clamp housing 104A includes features that mate and align it to distal clamp housing section 104B. Section 104 also acts as a guide for button 140. An opening 134 is located on the front surface to allow the user to press the button for endotracheal tube movement.

Button 140 is designed to reside within the clamp housing 104. It provides a means for a user to compress clamp springs 132 and allow the endotracheal tube to be inserted or removed. Button 140 also provides the proximal support for the clamp springs.

Blade 128 attaches to prong 114. Blade 128 punctures through the cricothyroid membrane, allowing adequate room for both prongs to follow.

Figure 20:
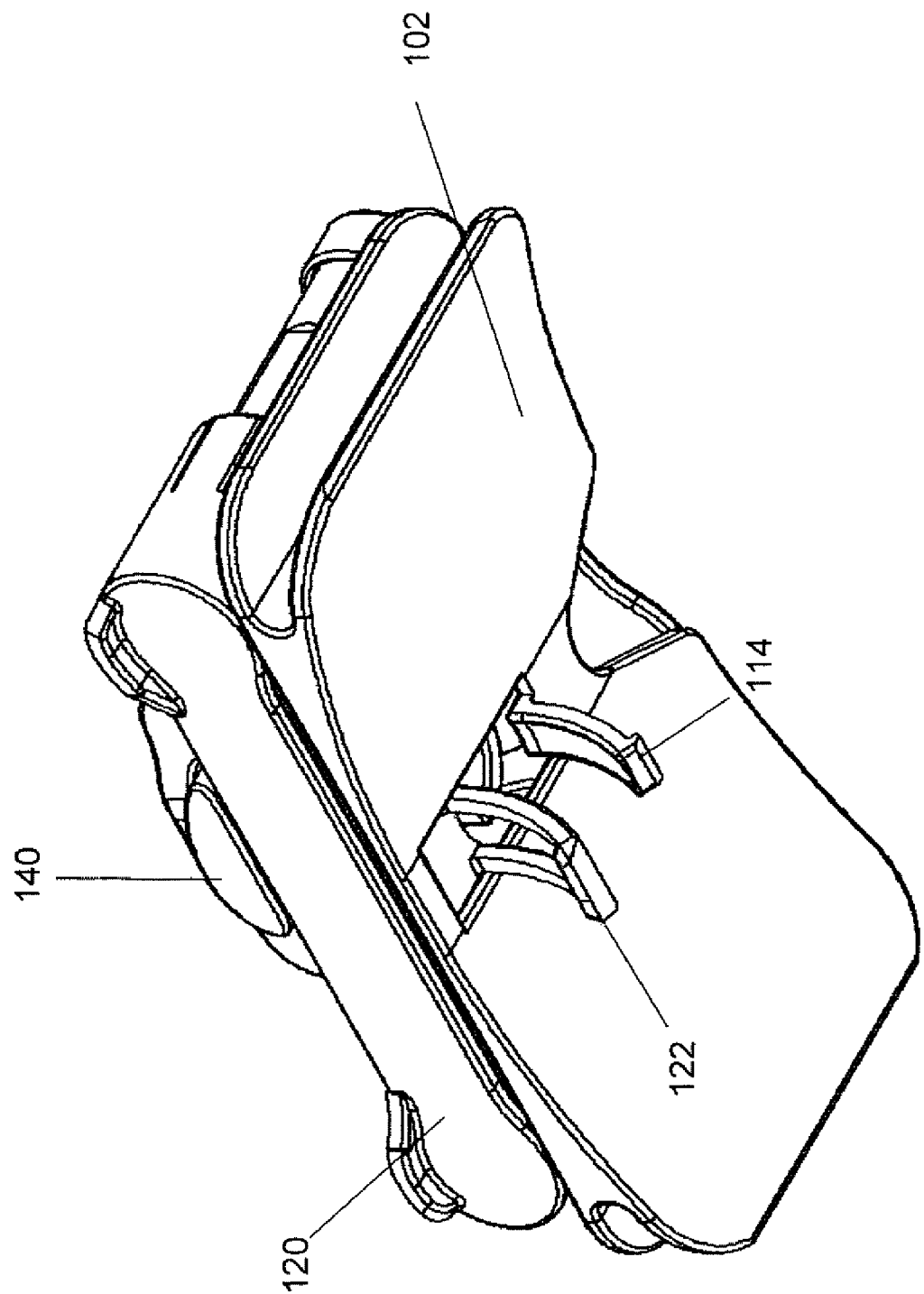
FIG. 20 is a bottom view of the device of FIG. 18.
Figure 21:
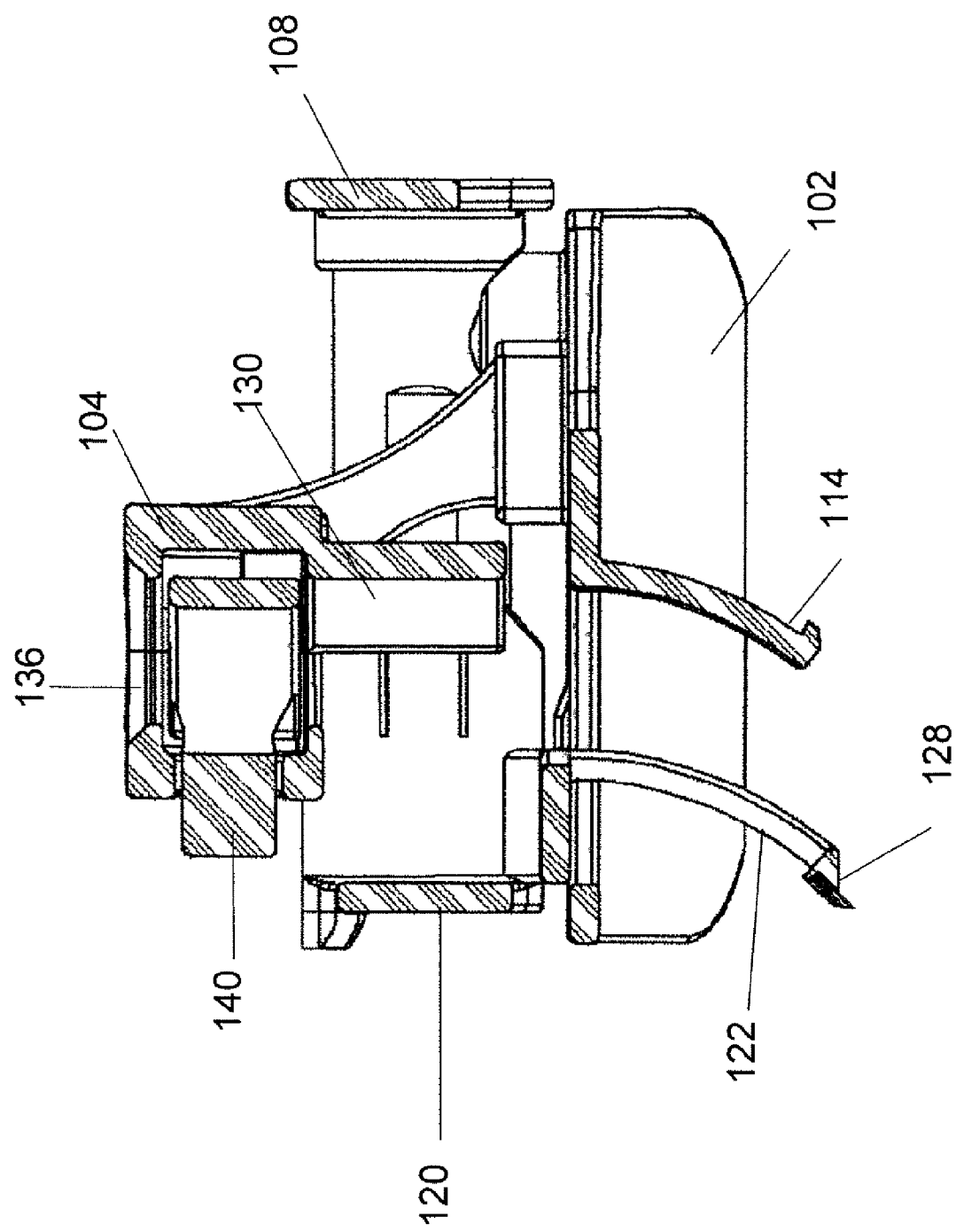
FIG. 21 is a side view of the device taken along line IV-IV of FIG. 18.
Figure 22:
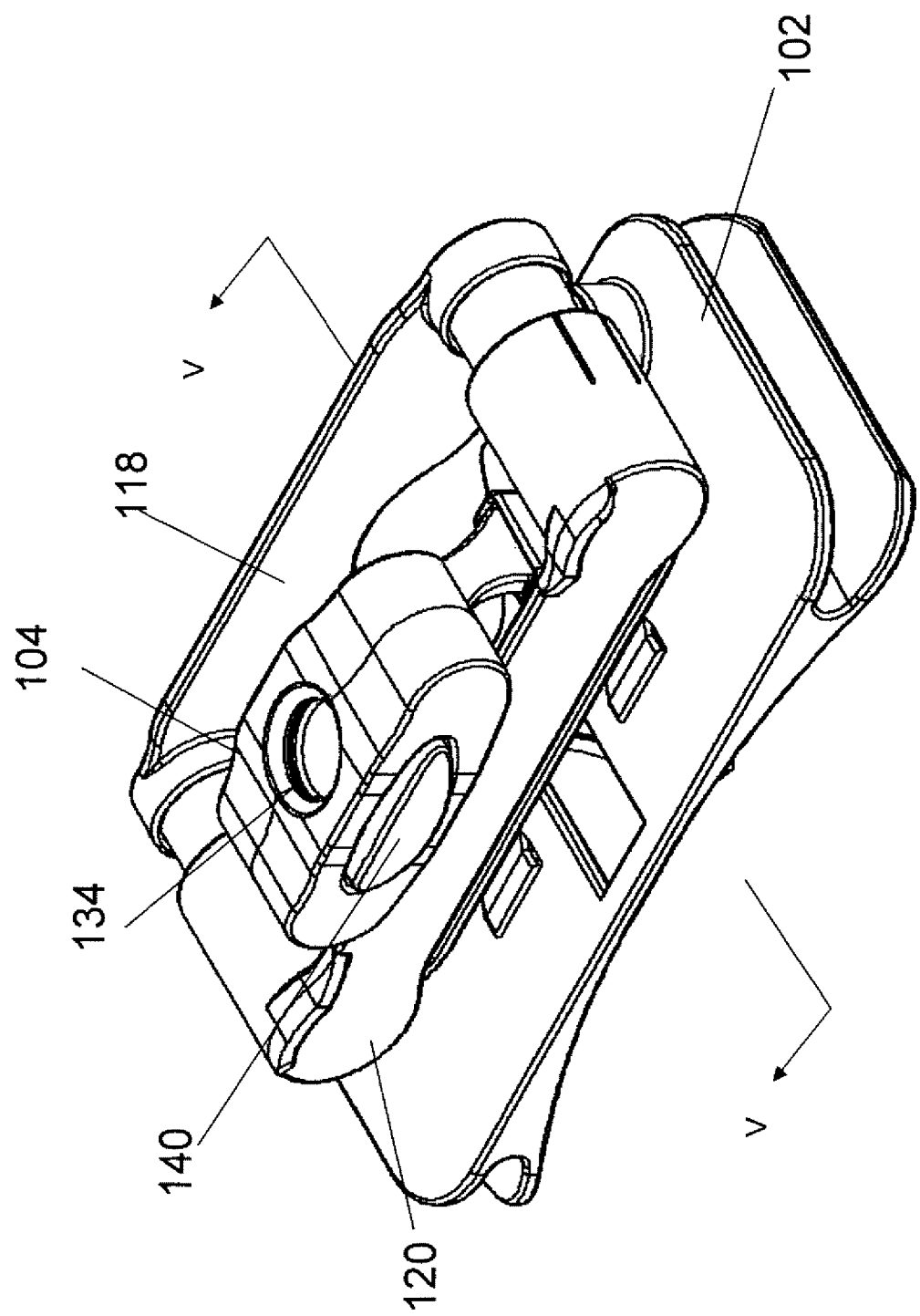
FIG. 22 is a perspective view of the device in a compressed position.
Figure 23:
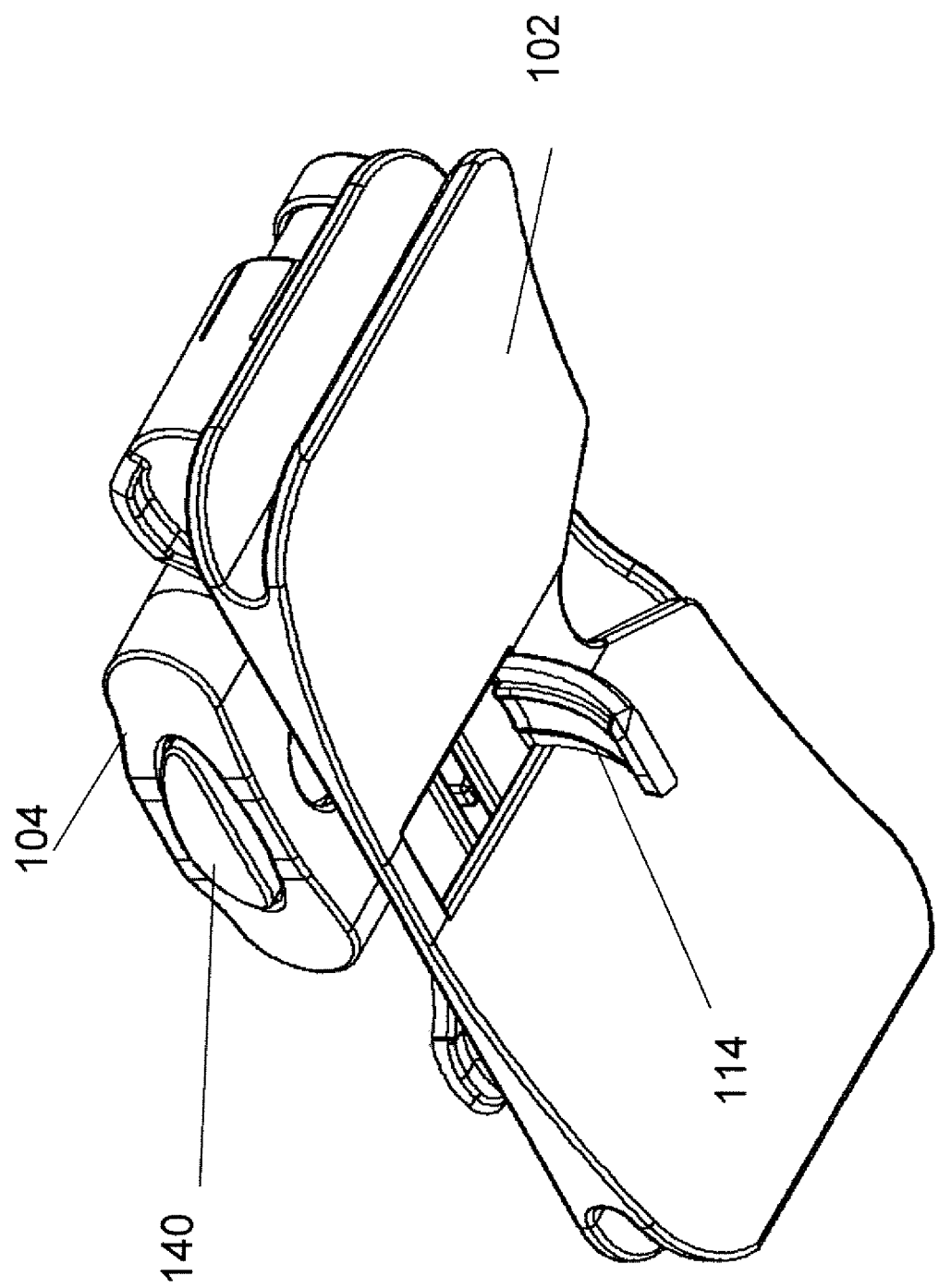
FIG. 23 is a bottom view of the device of FIG. 22.
Figure 24:
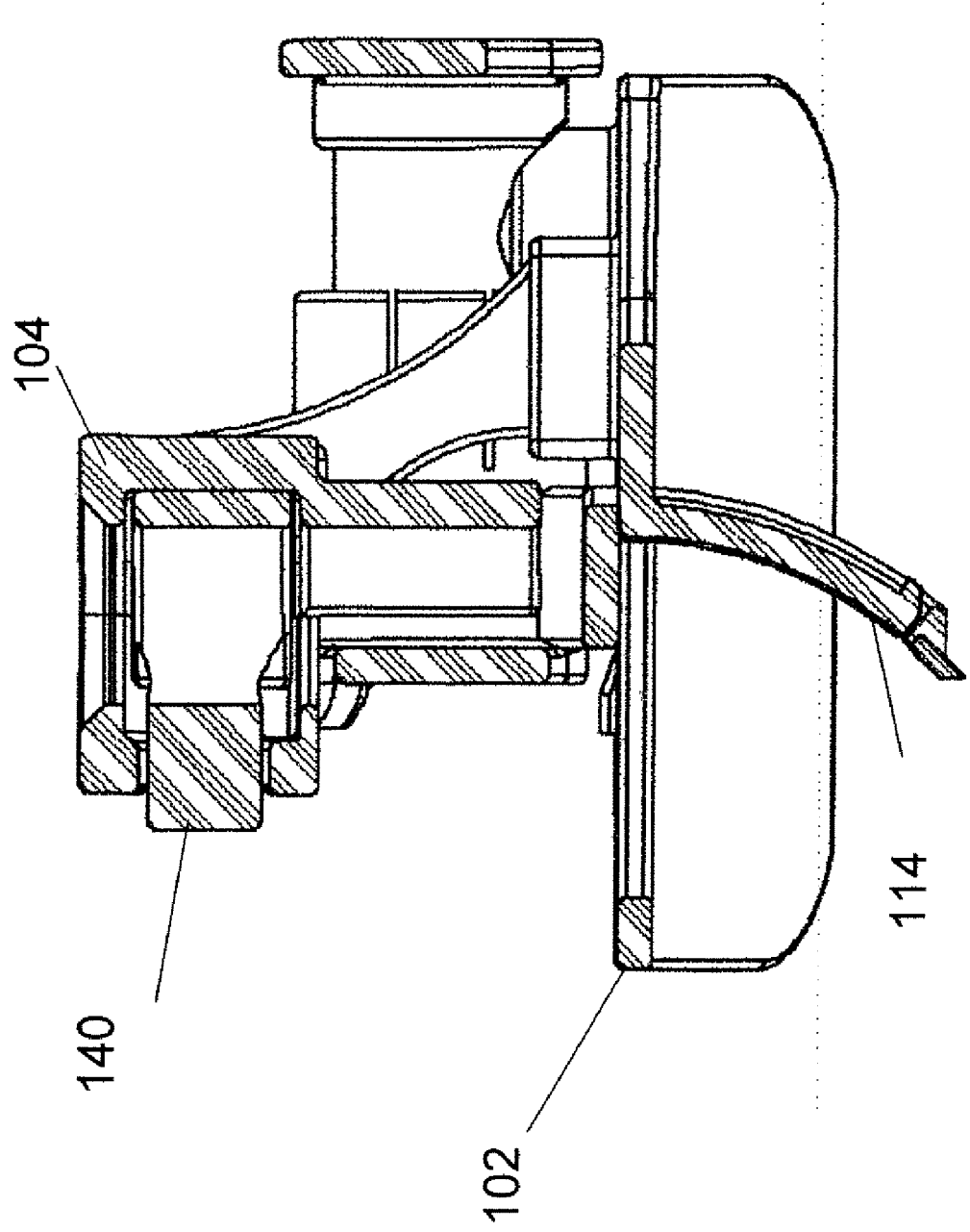
FIG. 24 is a side view of the device taken along line V-V of FIG. 22.

As shown in FIGS. 20-21, when the device is in a released position the prongs 114 and 122 are separated. As shown in FIGS. 23 and 24, and as described above, in the compressed position of the device prong 114 is received within prong 122 when the push plate 120 is compressed by the user. At that point the blade can be inserted into the cricothyroid membrane. Upon release of the device the prongs separate and an endotracheal tube can be inserted through opening 136, guide 130 and out between prongs 122 and 114. A mechanism can also be provided to secure an endotracheal tube to the device.

Although the present invention has been described in relation to particular embodiments thereof, many other variations and modifications and other uses will become apparent to those skilled in the art. It is preferred therefore, that the present invention be limited not by the specific disclosure herein, but only by the appended claims.

What is claimed:

1. A percutaneous emergent cricothyroidotomy airway device comprising:
   a housing;
   a palm grip movably disposed in the housing between an expanded position and a compressed position;
   a first prong extending from the housing;
   a second prong extending from said palm grip, wherein when said palm grip is in the expanded position said first and second prongs are spaced apart and when said palm grip is moved to the compressed position said second prong is adjacent said first prong;
   a blade actuator movably disposed in the housing, said blade actuator having opposed ends; and
   a blade for puncturing a cricothyroid membrane of a patient disposed on one end of said blade actuator.

2. The airway device of claim 1, wherein said blade is positioned between said first and second prongs.

3. The airway device of claim 2, wherein said blade actuator is constructed and arranged in said housing to move the blade between a retracted position wherein the blade is located within the housing and a released position wherein the blade extends from between said first and second prongs.

4. The airway device of claim 3, further comprising a blade actuator spring disposed in said blade actuator, wherein said blade actuator provides an upward force on said blade actuator to maintain the blade in said retracted position within the housing.

5. The airway device of claim 1, further comprising at least one incision expansion spring located between the housing and said palm grip, wherein when said palm grip is moved inward into the housing to the compressed position said at least one incision expansion spring is compressed and said second prong is moved adjacent said first prong.

6. The airway device of claim 5, wherein said at least one incision expanding spring has a force capable of separating the first and second prongs when the palm grip is in the released position.

7. The airway device of claim 1, wherein when the palm grip is in the compressed position said first and second prongs are adjacent to each other forming a tissue separator having a blunt tip that aids a user to locate a cricothyroid membrane notch of a patient.

8. The airway device of claim 7, wherein the blade has a sharpened tip that can puncture the cricothyroid membrane to enable a user to insert the tissue separator.

9. The airway device of claim 1, further comprising a button disposed on the other end of the blade actuator, wherein the blade actuator acts as a linkage between a user's thumb and the blade.

10. The airway device of claim 1, wherein the housing includes a passageway having opposed ends for receiving an endotracheal tube.

11. The airway device of claim 10, further comprising a cap located on the housing, the cap having a first and second opening.

12. The airway device of claim 11, wherein the button extends from the first opening and said second opening is aligned with one end of the passageway to receive the endotracheal tube.

13. The airway device of claim 12, wherein the other end of the passageway communicates with a space between said spaced first and second prongs such that the endotracheal tube can pass from the device, between the prongs and into the patient's airway.

14. The airway of claim 1, wherein the housing has an ergonomic shape.

15. The airway device of claim 1, wherein the first prong is formed of the housing and the second prong is formed of the palm grip.

16. A method for creating a percutaneous emergent cricothyroidotomy airway comprising the steps of:
   providing an airway device, the device having a housing, a palm grip movably disposed in the housing between an expanded position and a compressed position, a first prong extending from the housing, a second prong extending from said palm grip, wherein when said palm grip is in the expanded position said first and second prongs are spaced apart and when said palm grip is moved to the compressed position said second prong is adjacent said first prong, a blade actuator movably disposed in the housing, said blade actuator having opposed ends, and a blade disposed between the first and second prongs for puncturing a cricothyroid membrane of a patient disposed on one end of said blade actuator;
   compressing the palm grip to move the second prong adjacent said first prong;
   actuating the blade actuator to advance the blade from between the prongs;
   advancing the blade through the cricothyroid membrane to create an incision;
   retracting the blade;
   positioning the first and second prongs within the cricothyroid membrane; and
   releasing the palm grip to separate said first and second prongs to separate the tissue and form an airway.

17. The method of claim 16, further comprising the steps of:
    providing an endotracheal tube;
    advancing the endotracheal tube through the device between the first and prongs into the airway following the step of releasing the palm grip;
    removing the device; and
    leaving the endotracheal tube within the patient.

18. The method of claim 16, wherein the first prong is formed of the housing and the second prong is formed of the palm grip.

19. A percutaneous emergent cricothyroidotomy airway device comprising:
    a housing;
    a palm grip movably disposed in the housing between an expanded position and a compressed position;
    a first prong extending from the housing;
    a second prong extending from said palm grip, wherein when said palm grip is in the expanded position said first and second prongs are spaced apart and when said palm grip is moved to the compressed position said second prong is adjacent said first prong;
    a blade actuator movably disposed in the housing, said blade actuator having opposed ends;
    a blade for puncturing a cricothyroid membrane of a patient disposed on one end of said blade actuator; and
    at least one incision expansion spring located between the housing and said palm grip, wherein when said palm grip is moved inward into the housing to the compressed position said at least one incision expansion spring is compressed and said second prong is moved adjacent said first prong, wherein said at least one incision expanding spring has a force capable of separating the first and second prongs when the palm grip is in the released position.

20. The airway device of claim 19, wherein said blade is positioned between said first and second prongs.

21. The airway device of claim 20, wherein said blade actuator is constructed and arranged in said housing to move the blade between a retracted position wherein the blade is located within the housing and a released position wherein the blade extends from between said first and second prongs.

22. The airway device of claim 21, further comprising a blade actuator spring disposed in said blade actuator, wherein said blade actuator provides an upward force on said blade actuator to maintain the blade in said retracted position within the housing.

23. The airway device of claim 19, wherein when the palm grip is in the compressed position said first and second prongs are adjacent to each other forming a tissue separator having a blunt tip that aids a user to locate a cricothyroid membrane notch of a patient.

24. The airway device of claim 23, wherein the blade has a sharpened tip that can puncture the cricothyroid membrane to enable a user to insert the tissue separator.

25. The airway device of claim 19, further comprising a button disposed on the other end of the blade actuator, wherein the blade actuator acts as a linkage between a user's thumb and the blade.

26. The airway device of claim 19, wherein the housing includes a passageway having opposed ends for receiving an endotracheal tube.

27. The airway device of claim 26, further comprising a cap located on the housing, the cap having a first and second opening.

28. The airway device of claim 27, wherein the button extends from the first opening and said second opening is aligned with one end of the passageway to receive the endotracheal tube.

29. The airway device of claim 28, wherein the other end of the passageway communicates with a space between said spaced first and second prongs such that the endotracheal tube can pass from the device, between the prongs and into the patient's airway.

30. The airway of claim 19, wherein the housing has an ergonomic shape.

31. A percutaneous emergent cricothyroidotomy airway device comprising:
    a housing which includes a passageway having opposed ends for receiving an endotracheal tube and a cap located on the housing, the cap having a first and second opening;
    a palm grip movably disposed in the housing between an expanded position and a compressed position;
    a first prong extending from the housing;
    a second prong extending from said palm grip, wherein when said palm grip is in the expanded position said first and second prongs are spaced apart and when said palm grip is moved to the compressed position said second prong is adjacent said first prong;
    a blade actuator movably disposed in the housing, said blade actuator having opposed ends;
    a blade for puncturing a cricothyroid membrane of a patient disposed on one end of said blade actuator; and
    a button disposed on the other end of the blade actuator, wherein the button extends from the first opening of the cap and said second opening of the cap is aligned with one end of the passageway to receive the endotracheal tube and the other end of the passageway communicates with a space between said spaced first and second prongs such that the endotracheal tube can pass from the device, between the prongs and into the patient's airway, wherein the blade actuator acts as a linkage between a user's thumb and the blade.

32. The airway device of claim 31, wherein said blade is positioned between said first and second prongs.

33. The airway device of claim 32, wherein said blade actuator is constructed and arranged in said housing to move the blade between a retracted position wherein the blade is located within the housing and a released position wherein the blade extends from between said first and second prongs.

34. The airway device of claim 33, further comprising a blade actuator spring disposed in said blade actuator, wherein said blade actuator provides an upward force on said blade actuator to maintain the blade in said retracted position within the housing.

35. The airway device of claim 31, further comprising at least one incision expansion spring located between the housing and said palm grip, wherein when said palm grip is moved inward into the housing to the compressed position said at least one incision expansion spring is compressed and said second prong is moved adjacent said first prong.

36. The airway device of claim 35, wherein said at least one incision expanding spring has a force capable of separating the first and second prongs when the palm grip is in the released position.

37. The airway device of claim 31, wherein when the palm grip is in the compressed position said first and second prongs are adjacent to each other forming a tissue separator having a blunt tip that aids a user to locate a cricothyroid membrane notch of a patient.

38. The airway device of claim 37, wherein the blade has a sharpened tip that can puncture the cricothyroid membrane to enable a user to insert the tissue separator.

39. The airway of claim 31, wherein the housing has an ergonomic shape.

* * * * *